(12) United States Patent
Zhang

(10) Patent No.: US 9,617,279 B1
(45) Date of Patent: Apr. 11, 2017

(54) IMIDAZOOXADIAZOLE COMPOUNDS

(71) Applicant: BRISTOL-MYERS SQUIBB COMPANY, Princeton, NJ (US)

(72) Inventor: Xiaojun Zhang, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/747,037

(22) Filed: Jun. 23, 2015

Related U.S. Application Data

(60) Provisional application No. 62/016,161, filed on Jun. 24, 2014.

(51) Int. Cl.
| | |
|---|---|
| *C07D 271/12* | (2006.01) |
| *C07D 498/04* | (2006.01) |
| *A61K 31/4245* | (2006.01) |
| *A61K 31/5377* | (2006.01) |
| *A61K 31/454* | (2006.01) |
| *A61K 31/4439* | (2006.01) |
| *A61K 31/506* | (2006.01) |

(52) U.S. Cl.
CPC ........ *C07D 498/04* (2013.01); *A61K 31/4245* (2013.01); *A61K 31/4439* (2013.01); *A61K 31/454* (2013.01); *A61K 31/506* (2013.01); *A61K 31/5377* (2013.01)

(58) Field of Classification Search
CPC .................................................... C07D 271/12
See application file for complete search history.

(56) References Cited

U.S. PATENT DOCUMENTS

| | | | |
|---|---|---|---|
| 6,673,815 B2 | 1/2004 | Devasthale et al. | |
| 2015/0094297 A1 | 4/2015 | Banville et al. | |
| 2015/0119390 A1 | 4/2015 | Martel et al. | |
| 2015/0133446 A1 | 5/2015 | Lawrence et al. | |

FOREIGN PATENT DOCUMENTS

| | | |
|---|---|---|
| CA | 2 584 745 A1 | 10/2007 |
| EP | 0 005 783 A1 | 12/1979 |
| EP | 0 158 012 A1 | 10/1985 |
| EP | 0 185 345 A1 | 6/1986 |
| EP | 0 299 209 A2 | 1/1989 |
| EP | 0 379 979 A1 | 8/1990 |
| EP | 2 518 066 A1 | 10/2012 |
| WO | WO 01/27118 A2 | 4/2001 |
| WO | WO 01/27119 A2 | 4/2001 |
| WO | WO 01/81344 A1 | 11/2001 |
| WO | WO 03/040114 A1 | 5/2003 |
| WO | WO 03/051890 A1 | 6/2003 |
| WO | WO 2005/080355 A1 | 9/2005 |
| WO | WO 2008/104279 A1 | 9/2008 |
| WO | WO 2008/141249 A1 | 11/2008 |
| WO | WO 2009/017954 A1 | 2/2009 |
| WO | WO 2009/023179 A2 | 2/2009 |
| WO | WO 2009/027733 A1 | 3/2009 |
| WO | WO 2009/079683 A1 | 7/2009 |
| WO | WO 2010/075376 A2 | 7/2010 |
| WO | WO 2011/074658 A1 | 6/2011 |
| WO | WO 2013/163244 A1 | 10/2013 |
| WO | WO 2013/163279 A1 | 10/2013 |
| WO | WO 2014/015167 A2 | 1/2014 |

OTHER PUBLICATIONS

Becker et al, 2008, Antithrombotic and Thrombolytic Therapy 8th Ed: Accp Guidelines, 776S-814S.*
Abdel-Wahab, B.F. et al., "Synthesis of New 2-Naphthyl Ethers and Thier Protective Activities against DNA Damage Induced by Bleomycin-Iron", Chem. Pharm. Bull., vol. 57, No. 12, pp. 1348-1351 (2009).
Barlin, G.B. et al., "Imidazo[1,2-*b*]pyridazines, XIII, Synthesis and Central Nervous System Activites of Some 2-Benzyl(phenethyl, biphenyl-4'-yl, 6'-methylnaphthalen-2'-yl, t-butyl and cyclohexl)-3-methoxy(acylaminomethyl and dimethylaminomethyl)-6-(variously substituted)imidazo[1,2-*b*]pyridazines", Aust. J. Chem., vol. 45, pp. 1281-1300 (1992).
Bhovi, V.K. et al., "Synthesis of Some Mannich Bases and Novel Benzofuran Derivatives Containing Imidazo[2,1-b][1,3,4]thiadiazoles as Biological Agents" Current Chemical Biology, vol. 4, No. 2, pp. 145-150 (2010).
CAS Registry No. 1096958-08-5. Entered STN: Jan. 28, 2009.
CAS Regstry No. 1097016-53-9, Entered STN: Jan. 28, 2009.
CAS Registry No. 1097037-01-8, Entered STN: Jan. 28, 2009.
CAS Registry No. 1097163-93-3, Entered STN: Jan. 28, 2009.
Rani, R. et al., "Microwave Assisted Facile Synthesis and Antimicrobial Activity of Some New Imidazo[2,1-*b*]-1,3,4-thiadiazoles", Indian Journal of Heterocyclic Chemistry, vol. 18, pp. 121-124 (2008).
Tegginamath, G. et al., "Synthesis of novel imidazo[2,1-*b*][1,3,4]thiadiazoles appended to sydnone as anticancer agents", Medicinal Chemistry Research; vol. 22, pp. 4367-4375 (2013).
Martel et al., U.S. Appl. No. 14/746,908, filed Jun. 23, 2015.

* cited by examiner

*Primary Examiner* — Rebecca Anderson
*Assistant Examiner* — Karen Cheng
(74) *Attorney, Agent, or Firm* — Mary K. VanAtten

(57) ABSTRACT

The present invention provides thiazole compounds of Formula I

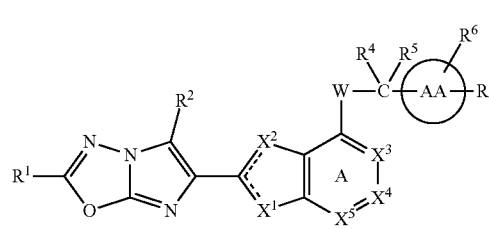

wherein $X^1$, $X^2$, $X^3$, $X^4$, $X^5$, $R^1$, $R^2$, $R^4$, $R^5$, $R^6$, $R^7$, and W, and ring AA, are as defined herein, or a stereoisomer, tautomer, pharmaceutically acceptable salt, prodrugs, or esters or solvate form thereof, wherein all of the variables are as defined herein. These compounds are inhibitors of platelet aggregation and thus can be used as medicaments for treating or preventing thromboembolic disorders.

15 Claims, No Drawings

IMIDAZOOXADIAZOLE COMPOUNDS

CROSS-REFERENCE TO RELATED APPLICATIONS

This application claims priority to U.S. Provisional Application Ser. No. 62/016,161, filed Jun. 24, 2014, the entire content of which is incorporated herein by reference.

FIELD OF THE INVENTION

The present invention provides novel imidazooxadiazole inhibitors of platelet aggregation which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

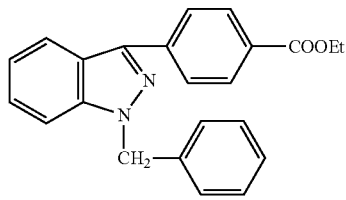

58

"was found to be a selective and potent inhibitor of protease-activated receptor type 4 (PAR4)-dependent platelet activation."

Compound 58 is also referred to as YD-3 in Wu, C-C. et al., "Selective Inhibition of Protease-activated Receptor 4-Dependent Platelet Activation by YD-3", *Thromb. Haemost.*, 87:1026-1033 (2002). Also, see Chen, H. S. et al., "Synthesis and antiplatelet activity of ethyl 4-(1-benzyl-1H-indazol-3-yl)benzoate (YD-3) derivatives", *Bioorg. Med. Chem.*, 16:1262-1278 (2008).

EP1166785 A1 and EP0667345 disclose various pyrazole derivatives which are useful as inhibitors of platelet aggregation.

The PCT publications WO2013/163279, WO2013/163244, and WO2013/163241 disclose various PAR4 antagonists which are useful as inhibitors of platelet aggregation.

SUMMARY OF THE INVENTION

It has been found that imidazooxadiazole compounds in accordance with the present invention are PAR4 antagonists which inhibit platelet aggregation in gamma-thrombin induced platelet aggregation assays.

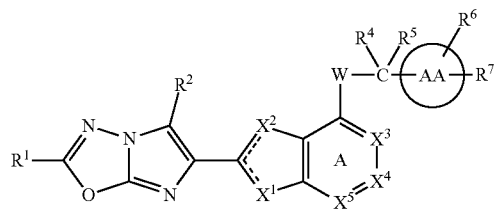

I

Accordingly, the present invention provides novel imidazooxadiazole analogues which are PAR4 antagonists and are useful as selective inhibitors of platelet aggregation, including stereoisomers, tautomers, pharmaceutically acceptable salts, solvates, or prodrugs, or esters thereof.

The present invention also provides processes and intermediates for making the compounds of the present invention or stereoisomers, tautomers, pharmaceutically acceptable salts, solvates, or prodrugs, or esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs, or esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs, or esters thereof.

The present invention also provides the compounds of the present invention or stereoisomers, tautomers, pharmaceutically acceptable salts, solvates, or prodrugs, or esters thereof, for use in therapy.

The present invention also provides the use of the compounds of the present invention or stereoisomers, tautomers, pharmaceutically acceptable salts, solvates, or prodrugs, or esters thereof, for the manufacture of a medicament for the treatment or prophylaxis of a thromboembolic disorder.

Other features and advantages of the invention will be apparent from the following detailed description and claims.

DETAILED DESCRIPTION

In one embodiment, the present invention provides imidazooxazole compounds, stereoisomers, tautomers, salts, solvates or prodrugs thereof, of Formula I having the structure:

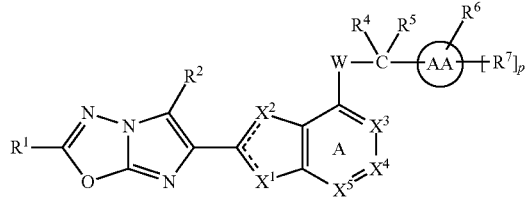

I wherein:
the dashed line represents an optional double-bond
$X^1$ is O and $X^2$ is CH, $CR^{10}$, or N; or
$X^1$ is N and $X^2$ is O; or
$X^1$ is N, CH, or $CR^{10}$, and $X^2$ is S; or
$X^1$ is N and $X^2$ is NH; or
$X^1$ is NH and $X^2$ is CH or $CR^{10}$; or
$X^1$ is CH or $CR^{10}$ and $X^2$ is NH;
$X^3$, $X^4$ and $X^5$ are independently selected from $CR^3$ or N;
W is O or S;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—,
halo-$C_1$-$C_2$-alkyl, where halo is F or Cl,
halo-$C_3$-$C_4$ cycloalkyl,
halo-$C_1$-$C_2$ alkoxy, and
halo-$C_1$-$C_2$ alkylthio;
$R^2$ is selected from the group consisting of:
H,
halo,
$C_1$-$C_4$ alkyl,
$C_1$-$C_4$ alkoxy, and
halo-$C_1$-$C_2$-alkyl, where halo is F or Cl, and
cyano;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —(CH$_2$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H, $C_1$-$C_6$ alkyl, $C_{1-4}$ hydroxyalkyl, $C_{1-4}$ fluoroalkyl or $R^4$ and $R^5$ can be taken together with the carbon to which they are attached to form a $C_3$-$C_7$ cycloalkyl ring;

is selected from the group consisting of a phenyl ring, a 5-membered heteroaryl ring containing at least one O, N or S atom, or a 6-membered heteroaryl ring, containing at least one nitrogen atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where
D is a linker, which is selected from a single bond, —O—, —S—,

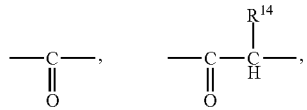

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, and $C_2$-$C_6$ alkenylene,
B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_5$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;
$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —$(CHR^{13})_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —$(CHR^{13})_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR^{11}R^{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl.

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—$(CR^{14}R^{14})_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
$C_1$-$C_4$-alkyleneoxy-$C_1$-$C_4$-alkylene,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_1$-$C_4$-alkoxy, and halo-$C_1$-$C_4$-alkoxy;

or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

the dashed line represents an optional double-bond
$X^1$ is O and $X^2$ is CH, $CR^{10}$, or N; or
$X^1$ is N and $X^2$ is O; or
$X^1$ is N, CH, or $CR^{10}$, and $X^2$ is S; or
$X^1$ is N and $X^2$ is NH; or
$X^1$ is NH and $X^2$ is CH or $CR^{10}$; or
$X^1$ is CH or $CR^{10}$ and $X^2$ is NH;
$X^3$, $X^4$ and $X^5$ are independently selected from $CR^3$ or N;
W is O or S;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—, halo-$C_1$-$C_2$-alkyl, where halo is F or Cl,
halo-$C_3$-$C_4$ cycloalkyl,
halo-$C_1$-$C_2$ alkoxy, and
halo-$C_1$-$C_2$ alkylthio;

$R^2$ is selected from the group consisting of:
H,
halo,
$C_1$-$C_4$ alkyl,
$C_1$-$C_4$ alkoxy, and
halo-$C_1$-$C_2$-alkyl, where halo is F or Cl, and cyano;

$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H, $C_1$-$C_6$ alkyl, $C_{1-4}$ hydroxyalkyl, $C_{1-4}$ fluoroalkyl or $R^4$ and $R^5$ can be taken together with the carbon to which they are attached to form a $C_3$-$C_7$ cycloalkyl ring;

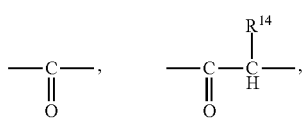

is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where
D is a linker, which is selected from a single bond, —O—, —S—, $$-\underset{O}{\overset{}{C}}-, \quad -\underset{O}{\overset{R^{14}}{\underset{|}{C}}}-\underset{H}{\overset{}{C}}-,$$

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O)— and —C(=O)NH—, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; $R^{10}$ is selected from the group consisting of $C_1$-$C_4$ alkyl, halo, cyano, $C_1$-$C_4$ alkoxy, and halo-$C_1$-$C_2$-alkyl, where halo is F or Cl.

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—(CR$^{14}$R$^{14}$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;
$R^{13}$ is independently, at each occurrence, selected from the group consisting of H, $C_1$-$C_6$ alkyl and —$(CH_2)$ phenyl;
$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_1$-$C_4$-alkoxy, and halo-$C_1$-$C_4$-alkoxy
or $R^6$ and $R^7$ can be taken together with the carbons to which they attach to form a $C_6$-$C_{10}$ aryl ring;
n, at each occurrence, is selected from 0, 1, 2, 3, 4 or 5; and
p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

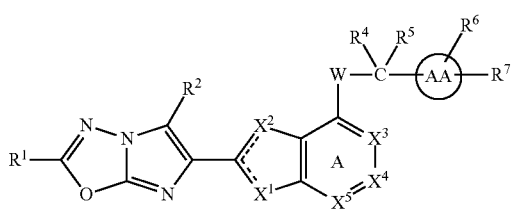

I wherein:
the dotted line represents a single or double bond;
$X^1$ is O and $X^2$ is CH, $CR^{10}$, or N; or
$X^1$ is N and $X^2$ is NH; or
$X^1$ is NH and $X^2$ is CH or $CR^{10}$; or
$X^1$ is CH or $CR^{10}$ and $X^2$ is NH;
$X^3$, $X^4$ and $X^5$ are independently selected from $CR^3$ or N;
W is O;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—,
halo-$C_1$-$C_2$-alkyl, where halo is F or Cl,
halo-$C_3$-$C_4$ cycloalkyl,
halo-$C_1$-$C_2$ alkoxy, and
halo-$C_1$-$C_2$ alkylthio;
$R^2$ is H;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H, $C_1$-$C_6$ alkyl, $C_1$-$C_4$ fluoroalkyl or $R^4$ and $R^5$ can be taken together with the carbon to which they are attached to form a $C_3$-$C_7$ cycloalkyl ring;

(AA)

is selected from the group consisting of a phenyl ring, a 5-membered heteroaryl ring containing at least one O, N or S atom, or a 6-membered heteroaryl ring, containing at least one nitrogen atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or R⁶ is B-D-, where
D is a linker, which is selected from a single bond, —O—, —S—,

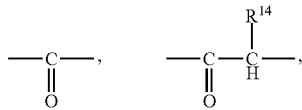

C₁-C₄ alkylene substituted by 0 to 4 groups independently selected from halo or OH, C₁-C₄ alkyleneoxy, C₁-C₄ alkylenethio, C₁-C₄ alkyleneoxy-C₁-C₄-alkylene, C₁-C₄-alkylenethio-C₁-C₄-alkylene, —S—C₁-C₄-alkylene, —O—C₁-C₄-alkylene, and C₂-C₆ alkenylene, B is selected from the group consisting of a C₆-C₁₀ aryl, a 5- to 10-membered heteroaryl, a 4- to 10-membered heterocyclyl containing carbon atoms and 1 to 4 additional heteroatoms selected from N, O, and S, a C₃-C₈ cycloalkyl which may contain unsaturation and a C₅-C₁₁ spirocycloalkyl which may contain unsaturation and optionally containing 1 to 3 heteroatoms selected from O, N or S, all of which may be optionally substituted with one or more R$^b$, R$^c$, R$^d$ and R$^e$;

R$^b$, R$^c$, R$^d$ and R$^e$, at each occurrence, are independently selected from the group consisting of halo, halo-C₁-C₄ alkoxy, OH, CN, NO₂, =O, NR¹¹R¹², COOH, C₁-C₄ alkoxy, C₁-C₄ alkylthio, C₁-C₄ alkoxycarbonyl, (C=O)NR¹¹R¹², C₁-C₄ alkoxy-C₁-C₄ alkoxy, C₁-C₄ alkylsulfonyl, C₁-C₄ alkylsulfinyl, S(=O)₂NR¹¹R¹², N(R¹³)(C=O)NR¹¹R¹², N(R¹³)(C=O)OR¹⁴, SO₂R¹⁴, N(R¹³)(C=O)R¹⁴, NR¹³S(O)R¹⁴, NR¹³SO₂R¹⁴, O(C=O)NR¹¹R¹², O(C=O)OR¹⁴, O(C=O)R¹⁴, (C=O)OR¹⁴, C₃-C₆ cycloalkyl, a 4- to 10-membered heterocyclyloxy; a C₁-C₅ alkyl substituted by 0 to 7 groups independently selected from halo, CF₃, OCF₃, OH, CN, hydroxy-C₁-C₄-alkyl, C₁-C₄ alkoxy, C₁-C₄ alkoxy-C₁-C₄ alkoxy, di-C₁-C₄-alkylaminophenyl-C₁-C₄-alkyl, (di-C₁-C₄-alkoxy-C₁-C₄-alkyl)C₁-C₄-alkyl, di-C₁-C₄-alkylamino, C₃-C₆-cycloalkyl, phenyl, C₁-C₄-alkoxyphenyl-C₁-C₄-alkoxy, 4- to 10-membered heterocyclyloxy, C₁-C₄-alkylcarbonyloxy and C₁-C₄ alkylthio; —(CHR¹³)$_n$-5- or 6-membered heteroaryl substituted by 0 to 3 groups independently selected from the group consisting of halo, C₁-C₄ alkoxy, C₁-C₄ alkyl, cyclopropyl, CF₃, OCF₃, and CF₂CH₃; —(CHR¹³)$_n$-4- to 10-membered-heterocyclyl substituted by 0 to 3 groups independently selected from the group consisting of halo, C₁-C₄ alkoxy, C₁-C₄ alkyl, cyclopropyl, CF₃, OCF₃, and CF₂CH₃; OH, hydroxy-C₁-C₄-alkyl, C₁-C₄ alkoxy, halo-C₁-C₄ alkoxy, di-C₁-C₄-alkylamino-C₁-C₄-alkyl, NR¹¹R¹², cyano, C₁-C₄ alkyl, halo-C₁-C₄ alkyl, C₃-C₆ cycloalkyl, C₁-C₄-alkoxy-C₁-C₄-alkyl, C₃-C₆ cycloalkyl-C₁-C₄-alkylcarbonyl, C₆-C₁₀ arylcarbonyl, C₁-C₄-alkylcarbonyloxy-C₁-C₄-alkyl, COOR¹⁴, SO₂R¹⁴, (C=O)NR¹¹R¹², SO₂NR¹¹R¹², N(R¹³)(C=O)NR¹¹R¹², N(R¹³)(C=O)OR¹⁴, N(R¹³)(C=O)R¹⁴, O(C=O)NR¹¹R¹², O(C=O)OR¹⁴, O(C=O)R¹⁴, (C=O)OR¹⁴, and a C₆-C₁₀ aryl substituted by 0 to 3 groups independently selected from the group consisting of halo, C₁-C₄ alkoxy, C₁-C₄ alkyl, cyclopropyl, C₁-C₄-alkoxycarbonyl, (C=O)NR¹¹R¹², CF₃, OCF₃, and CF₂CH₃;

R¹⁰ is selected from the group consisting of C₁-C₄ alkyl, halo, cyano, C₁-C₄ alkoxy, and halo-C₁-C₂-alkyl, where halo is F or Cl.

R¹¹ and R¹² are independently, at each occurrence, selected from the group consisting of:
H,
C₁-C₄ alkyl,
halo-C₁-C₄-alkyl,
C₂-C₄ alkenyl,
C₂-C₄ alkynyl,
—(CR¹⁴R¹⁴)$_n$-phenyl substituted by 0 to 3 groups independently selected from the group consisting of halo, C₁-C₄ alkoxy, C₁-C₄ alkyl, cyclopropyl, CF₃, OCF₃, 5- or 6-membered heteroaryl, OH, OCHF₂, di-C₁-C₄-alkylamino, and cyano,
—(CHR¹³)$_n$—C₃-C₆-cycloalkyl substituted by 0 to 3 groups independently selected from the group consisting of halo, CF₃, OCF₃, 5- or 6-membered heteroaryl, OH, hydroxy-C₁-C₄-alkyl, and C₁-C₄ alkyl,
—(CHR¹³)$_n$-4- to 10-membered-heterocyclyl substituted by 0 to 3 groups independently selected from the group consisting of halo, CF₃, OCF₃, 5- or 6-membered heteroaryl, OH, oxo, hydroxy-C₁-C₄-alkyl, and C₁-C₄ alkyl,
—(CHR¹³)$_n$-5- to 10-membered-heteroaryl substituted by 0 to 3 groups independently selected from the group consisting of halo, CF₃, OCF₃, 5- or 6-membered heteroaryl, OH, hydroxy-C₁-C₄-alkyl, and C₁-C₄ alkyl,
di-C₁-C₄-alkylamino-C₁-C₄-alkyl,
C₁-C₄-alkylcarbonylamino-C₁-C₄-alkyl,
di-C₁-C₄-alkoxy-C₁-C₄-alkyl,
di-C₁-C₄-alkylaminophenyl,
hydroxy-C₁-C₄-alkyl,
cyano-C₁-C₄-alkyl,
C₁-C₄-alkoxy-C₁-C₄-alkyl,
C₁-C₄-alkoxycarbonyl-C₁-C₄-alkyl,
C₁-C₄-alkoxycarbonyl,
C₁-C₄-alkylcarbonyl,
phenylcarbonyl;
C₁-C₄-alkoxycarbonylamino-C₁-C₄-alkylcarbonyl,
di-C₁-C₄-alkylamino-C₁-C₄-alkylcarbonyl,
amino-C₁-C₄-alkylcarbonyl,
4- to 10-membered-heterocyclyl-carbonyl, and
alternatively, R¹¹ and R¹², when attached to the same nitrogen, combine to form a 4- to 10-membered mono- or bicyclic heterocyclic ring containing carbon atoms substituted by 0 to 3 groups independently selected from the group consisting of halo, cyano, CF₃, CHF₂, OCF₃, OCHF₂, OCH₂F, 5- or 6-membered heteroaryl, OH, oxo, hydroxy-C₁-C₄-alkyl, C₁-C₄ alkyl and C₁-C₄ alkoxy, and 0 to 2 additional heteroatoms selected from N, NR¹³, O and S(O)$_p$;

R¹³ is independently, at each occurrence, selected from the group consisting of H, C₁-C₆ alkyl and —(CH₂) phenyl;

R¹⁴ is independently, at each occurrence, selected from the group consisting of H, C₁-C₆ alkyl, halo-C₁-C₄-alkyl, C₁-C₄-alkoxycarbonylamino, (C₆-C₁₀ arylcarbonylamino), (a 5- to 10-membered heteroarylcarbonylamino) and —(CH₂)$_n$phenyl substituted by 0 to 3 groups independently selected from the group consisting of halo, C₁-C₄ alkoxy, C₁-C₄ alkyl, cyclopropyl, CF₃, OCF₃, 5- or 6-membered heteroaryl, OH, OCHF₂, di-C₁-C₄-alkylamino, and cyano, R⁷ is selected from the group consisting of H, halo, hydroxyl, cyano, oxo, C₁-C₄ alkyl, hydroxy-C₁-C₄-alkyl, C₁-C₄-alkoxy-C₁-C₄-alkyl, halo-C₁-C₄-alkyl, C₁-C₄-alkoxy, and halo-C₁-C₄-alkoxy or R⁶ and R⁷ can be taken together with the carbons to which they attach to form a C₆-C₁₀ aryl ring;

n, at each occurrence, is selected from 0, 1, 2, 3, 4 or 5; and p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

$X^1$ is O and $X^2$ is CH, $CR^{10}$, or N; or
$X^1$ is N and $X^2$ is O; or
$X^1$ is N and $X^2$ is S;
$X^3$, $X^4$ and $X^5$ are independently selected from $CR^3$ or N;
W is O;
$R^1$ is independently selected from the group consisting of:
  halo,
  $C_1$-$C_4$ alkyl,
  $C_1$-$C_4$ alkoxy,
  $C_1$-$C_4$ alkylthio,
  halo-$C_1$-$C_2$-alkyl, where halo is F or Cl,
$R^2$ is H;
$R^3$ is selected from the group consisting of $C_1$-$C_4$ alkoxy, $C_1$-$C_4$ alkylthio, halo, $OCF_3$, $OCHF_2$, $OCH_2F$, or halo-$C_1$-$C_3$-alkyl;
$R^4$ and $R^5$ are independently selected from H, $C_1$-$C_6$ alkyl, $C_1$-$C_4$ fluoroalkyl or $R^4$ and $R^5$ can be taken together with the carbon to which they are attached to form a $C_3$-$C_7$ cycloalkyl ring;

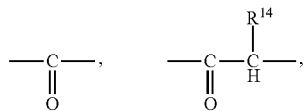

is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from a single bond, —O—, —S—, $$-\underset{\underset{O}{\|}}{C}-,\quad -\underset{\underset{O}{\|}}{C}-\underset{H}{\overset{R^{14}}{C}}-,$$

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, (C=O)$OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl.

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—(CR$^{14}$R$^{14}$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;
$R^{13}$ is independently, at each occurrence, selected from the group consisting of H, $C_1$-$C_6$ alkyl and —$(CH_2)$ phenyl;
$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_1$-$C_4$-alkoxy, and halo-$C_1$-$C_4$-alkoxy
or $R^6$ and $R^7$ can be taken together with the carbons to which they attach to form a $C_6$-$C_{10}$ aryl ring;
n, at each occurrence, is selected from 0, 1, 2, 3, 4 or 5; and
p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

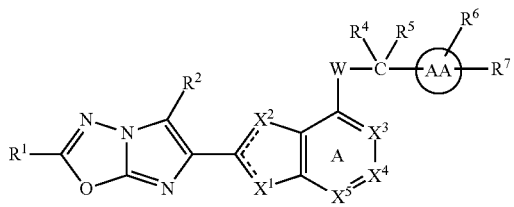

I wherein:
the dotted line represents a single or double bond;
X is O and $X^2$ is CH, $CR^{10}$, or N; or
$X^1$ is NH and $X^2$ is CH or $CR^{10}$; or
$X^1$ is CH or $CR^{10}$ and $X^2$ is NH;
$X^3$, $X^4$ and $X^5$ are each $CR^3$;
W is O;
$R^1$ is independently selected from the group consisting of:
halo,
$C_1$-$C_4$ alkyl,
$C_1$-$C_4$ alkoxy, and
halo-$C_1$-$C_2$-alkyl, where halo is F or Cl;
$R^2$ is H;
$R^3$ is selected from the group consisting of H, $C_1$-$C_4$ alkoxyhalo, $OCF_3$, $OCHF_2$, $OCH_2F$, and halo-$C_1$-$C_3$-alkyl;
$R^4$ and $R^5$ are independently selected from H, and $C_1$-$C_6$ alkyl;

is selected from the group consisting of a phenyl ring, a 5-membered heteroaryl ring containing at least one O, N or S atom, or a 6-membered heteroaryl ring, containing at least one nitrogen atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where
D is a linker, which is selected from a single bond, —O—, —S—,

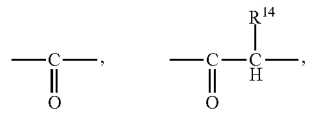

$C_1$-$C_4$ alkylene, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O)—, —C(=O)NH—, and $C_2$-$C_6$ alkenylene,
B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;
$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR^{11}R^{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl.

$R^{11}$ and $R^{12}$ are independently, at each occurrence, selected from the group consisting of:
H,
$C_1$-$C_4$ alkyl,
halo-$C_1$-$C_4$-alkyl, and tetrahydrofuranyl;

$R^{13}$ is independently, at each occurrence, selected from the group consisting of H, $C_1$-$C_6$ alkyl and —(CH$_2$) phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, and —(CH$_2$)$_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, cyano, oxo, $C_1$-$C_3$ alkyl, hydroxy-$C_1$-$C_3$-alkyl, and halo-$C_1$-$C_4$-alkyl;

or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

$X^1$ is O and $X^2$ is CH or N; or
  $X^1$ is N and $X^2$ is O; or
  $X^1$ is N and $X^2$ is S;
$X^3$, $X^4$ and $X^5$ are each $CR^3$;
W is O;
$R^1$ is independently selected from the group consisting of:
  halo,
  $C_1$-$C_4$ alkyl,
  $C_1$-$C_4$ alkoxy, and
  halo-$C_1$-$C_2$-alkyl, where halo is F or Cl;
$R^2$ is H;
$R^3$ is selected from the group consisting of H, $C_1$-$C_4$ alkoxy, $OCF_3$, $OCHF_2$, $OCH_2F$, and halo-$C_1$-$C_3$-alkyl;
$R^4$ and $R^5$ are independently selected from H, and $C_1$-$C_6$ alkyl;

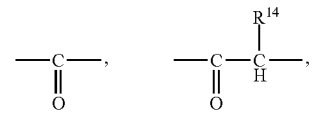

is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, $(C=O)NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where
D is a linker, which is selected from a single bond, —O—, —S—, $$-\overset{}{\underset{\parallel}{C}}-, \quad -\overset{}{\underset{\parallel}{C}}-\overset{R^{14}}{\underset{H}{C}}-,$$

$C_1$-$C_4$ alkylene, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O)—, —C(=O)NH—, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, $(C=O)NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —$(CHR^{13})_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —$(CHR^{13})_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl;

$R^{11}$ and $R^{12}$ are independently, at each occurrence, selected from the group consisting of:
H,
$C_1$-$C_4$ alkyl,
halo-$C_1$-$C_4$-alkyl,
—$(CR^{14}R^{14})_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
hydroxy-$C_1$-$C_4$-alkyl,
cyano-$C_1$-$C_4$-alkyl,
$C_1$-$C_4$-alkoxy-$C_1$-$C_4$-alkyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$ phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, and —$(CH_2)_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, cyano, oxo, $C_1$-$C_3$ alkyl, hydroxy-$C_1$-$C_3$-alkyl, and halo-$C_1$-$C_4$-alkyl;

or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

In still yet another embodiment, the present invention provides compounds, stereoisomers, tautomers, salts, solvates or prodrugs thereof, wherein the compounds are compounds of Formula I:

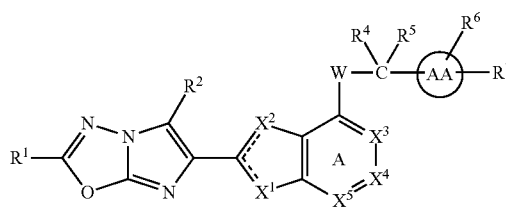

wherein
the dotted line represents a single or double bond;
$X^1$ is O and $X^2$ is CH;
$X^3$, and $X^5$ are each CH, and $X^4$ is $CR^3$;
W is O;
$R^1$ is independently selected from the group consisting of: H, $CH_3$, and $OCH_3$;
$R^2$ is H;
$R^3$ is selected from the group consisting of H, and $OCH_3$;
$R^4$ and $R^5$ are H;

(AA)

is selected from the group consisting of a phenyl, pyrimidinyl, and thiazolyl; $R^6$ is phenyl, morpholinyl, piperidinyl, all of which may be optionally substituted with one or more $R^b$, $R^c$, $R^d$ and $R^e$;

$R^b$, $R^c$, $R^d$ and $R^e$, at each occurrence, are independently selected from OH, $(C=O)NRR^{12}$, COOH, $(C=O)OR^{14}$, $R^{10}$ is selected from the group consisting of $C_1$-$C_4$ alkyl, halo, cyano, $C_1$-$C_4$ alkoxy, and halo-$C_1$-$C_2$-alkyl, where halo is F or Cl.

$R^{11}$ and $R^{12}$ are independently, at each occurrence, selected from the group consisting of:
H,
$C_1$-$C_4$ alkyl,
halo-$C_1$-$C_4$-alkyl, and tetrahydrofuranyl;

$R^{13}$ is independently, at each occurrence, selected from the group consisting of H, and $CH_3$;

R$^{14}$ is independently, at each occurrence, selected from the group consisting of H, and CH$_3$; R$^7$ is selected from the group consisting of H, or CH$_3$;
n, at each occurrence, is selected from 0, 1, or 2; and
p, at each occurrence, is selected from 0, 1 and 2.

In still yet another embodiment, the present invention provides compounds, stereoisomers, tautomers, salts, solvates or prodrugs thereof, wherein the compounds are compounds of Formula I:
X$^1$ is O and X$^2$ is CH;
X$^3$, and X$^5$ are each CH, and X$^4$ is CR$^3$;
W is O;
R$^1$ is independently selected from the group consisting of: CH$_3$, CH$_2$CH$_3$, CF$_2$CH$_3$, CHFCH$_3$, and OCH$_3$;
R$^2$ is H;
R$^3$ is OCH$_3$;
R$^4$ and R$^5$ are H;

is selected from the group consisting of phenyl, pyridyl, pyrimidinyl, pyrazinyl, and thiazolyl;
R$^6$ is selected from the group consisting of phenyl, cyclopentyl, cyclohexyl, pyridyl, morpholinyl, thiomorpholinyl, azetidinyl, pyrrolidinyl, piperidinyl, piperazinyl, azepanyl, tetrahydropyranyl, tetrahydrofuranyl, thiazolyl, oxazolyl, isoxazolyl, pyrazolyl, and imidazolyl, all of which may be optionally substituted with one or more R$^b$, R$^c$, R$^d$ and R$^e$;
R$^b$, R$^c$, R$^d$ and R$^e$, at each occurrence, are independently selected from halo, halo-C$_1$-C$_4$ alkoxy, OH, CN, NO$_2$, =O, NR$^{11}$R$^{12}$, COOH, C$_1$-C$_4$ alkoxy, C$_1$-C$_4$ alkylthio, C$_1$-C$_4$ alkoxycarbonyl, (C=O)NR$^{11}$R$^{12}$, C$_1$-C$_4$ alkylsulfonyl, C$_1$-C$_4$ alkylsulfinyl, S(=O)$_2$NR$^{11}$R$^{12}$, N(R$^{13}$)(C=O)NR$^{11}$R$^{12}$, N(R$^{13}$)(C=O)OR$^{14}$, SO$_2$R$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, and a C$_1$-C$_5$ alkyl substituted by 0 to 7 groups independently selected from halo and OH;
R$^{11}$ and R$^{12}$ are independently, at each occurrence, selected from the group consisting of:
H,
C$_1$-C$_4$ alkyl,
halo-C$_1$-C$_4$-alkyl,
cyclopropyl,
cyclopropylmethyl
hydroxy-C$_1$-C$_4$-alkyl,
cyano-C$_1$-C$_4$-alkyl,
C$_1$-C$_4$-alkoxy-C$_1$-C$_4$-alkyl,
oxetanyl,
tetrahydrofuranyl, and
alternatively, R$^{11}$ and R$^{12}$, when attached to the same nitrogen, combine to form an azetidine, pyrrolidine, piperidine, or azepane ring, substituted by 0 to 2 groups independently selected from the group consisting of halo, cyano, CF$_3$, CHF$_2$, OCF$_3$, OCHF$_2$, OCH$_2$F, OH, oxo, C$_1$-C$_4$ alkyl and C$_1$-C$_4$ alkoxy;
R$^{13}$ is independently, at each occurrence, selected from the group consisting of H, and CH$_3$;

R$^{14}$ is independently, at each occurrence, selected from the group consisting of H, and CH$_3$; R$^7$ is selected from the group consisting of H, F, or CH$_3$;
n, at each occurrence, is selected from 0, 1, or 2; and
p, at each occurrence, is selected from 0, 1 and 2.

In another embodiment, the present invention provides compounds, stereoisomers, tautomers, salts, solvates or prodrugs thereof, wherein W is O.

In another embodiment, the present invention provides compounds, stereoisomers, tautomers, salts, solvates or prodrugs thereof, of Formula Ia.

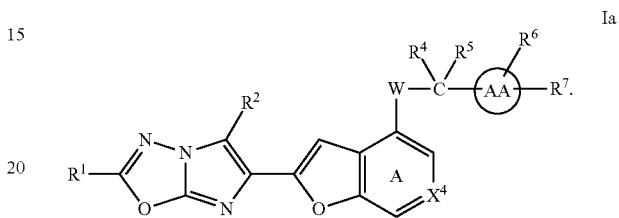

In another embodiment, the present invention provides compounds, stereoisomers, tautomers, salts, solvates or prodrugs thereof, of Formula I, or Ia,
wherein R$^1$ is C$_{1-3}$alkyl;
W is O;
X$^4$ is CR$^3$ or CH;
R$^3$ is C$_1$-C$_4$ alkoxy;
R$^4$ and R$^5$ are H;

is phenyl or thiazolyl, wherein the thiazolyl is substituted with R$^6$;
R$^6$ is H or B-D:
D is a single bond;
B is phenyl which may be optionally substituted with R$^b$;
R$^b$ is (C=O)NR$^{11}$R$^{12}$;
R$^{11}$ and R$^{12}$ are independently, at each occurrence, selected from the group consisting of:
H,
C$_1$-C$_4$ alkyl.

In still yet another embodiment, the present invention provides compounds, stereoisomers, tautomers, salts, solvates or prodrugs thereof, wherein the compounds are compounds of Formula I, or they are compounds of Formula Ia: or a stereoisomer, tautomer, pharmaceutically acceptable salt, solvate or prodrug thereof, wherein:
the dashed line represents an optional double-bond;
X is CR$^{1a}$ or N;
Y is CR$^{1a}$ or N;
Z is CR$^{1a}$ or N;
provided that at least one of X, Y, and Z is N, and provided that if X is N, then at least one of Y and Z is N;
X$^1$ is O and X$^2$ is CH;
X$^3$, and X$^5$ are CH, and X$^4$ is CR$^3$;
W is O;
R$^1$ is independently selected from the group consisting of: H, CH$_3$, and OCH$_3$;

$R^{1a}$ is selected from the group consisting of H, halo, $C_1$-$C_4$ alkyl, and $C_1$-$C_4$ alkoxy;
$R^2$ is H;
$R^3$ is selected from the group consisting of H, and $OCH_3$;
$R^4$ and $R^5$ are H;

(AA)

is selected from the group consisting of phenyl, pyrimidinyl, and thiazolyl;
$R^6$ is phenyl, morpholinyl, piperidinyl, all of which may be optionally substituted with one or more $R^b$, $R^c$, $R^d$ and $R^e$;
$R^b$, $R^c$, $R^d$ and $R^e$, at each occurrence, are independently selected from OH, (C=O)$NR^{11}R^{12}$, COOH, (C=O)$OR^{14}$,
$R^{11}$ and $R^{12}$ are independently, at each occurrence, selected from the group consisting of H; $C_1$-$C_4$ alkyl, halo-$C_1$-$C_4$-alkyl, and tetrahydrofuranyl; or
$R^{13}$ is independently, at each occurrence, selected from the group consisting of H, and $CH_3$;
$R^{14}$ is independently, at each occurrence, selected from the group consisting of H, and $CH_3$,
$R^7$ is selected from the group consisting of H, or $CH_3$;
n, at each occurrence, is selected from 0, 1, or 2; and
p, at each occurrence, is selected from 0, 1 and 2.

In still yet another embodiment, the present invention provides compounds, stereoisomers, tautomers, salts, solvates or prodrugs thereof, wherein the compounds are compounds of Formula I, or they are compounds of Formula Ia:
$X^1$ is O and $X^2$ is CH, $CR^{10}$, or N; or
$X^1$ is N and $X^2$ is NH; or
$X^1$ is NH and $X^2$ is CH or $CR^{10}$; or
$X^1$ is CH or $CR^{10}$ and $X^2$ is NH;
$X^3$, $X^4$ and $X^5$ are independently selected from $CR^3$ or N;
W is O.

In still yet another embodiment, the present invention provides compounds, stereoisomers, tautomers, salts, solvates or prodrugs thereof, wherein the compounds are compounds of Formula Ia:
$X^1$ is O and $X^2$ is CH, $CR^{10}$, or N; or
$X^1$ is NH and $X^2$ is CH or $CR^{10}$; or
$X^1$ is CH or $CR^{10}$ and $X^2$ is NH;
in ring A, $X^3$, $X^4$ and $X^5$ are independently selected from $CR^3$; W is O.

In still yet another embodiment, the present invention provides compounds, stereoisomers, tautomers, salts, solvates or prodrugs thereof, wherein the compounds are compounds of Formula Ia:
$X^1$ is O and $X^2$ is CH;
in ring A, $X^3$ and $X^5$ are CH, and $X^4$ is $CR^3$;
W is O.

In still yet another embodiment, the present invention provides compounds, stereoisomers, tautomers, salts, solvates or prodrugs thereof, wherein the compounds are compounds of Formula Ia:
$R^2$ is H.

In still yet another embodiment, the present invention provides compounds, stereoisomers, tautomers, salts, solvates or prodrugs thereof, wherein the compounds are compounds of Formula Ia:
$R^1$ is independently selected from the group consisting of: H, $CH_3$, and $OCH_3$.

In still yet another embodiment, the present invention provides compounds, stereoisomers, tautomers, salts, solvates or prodrugs thereof, wherein the compounds are compounds of Formula I, or they are compounds of Formula Ia:
$R^1$ is independently selected from the group consisting of: $CH_3$ and $CH_2CH_3$.

In still yet another embodiment, the present invention provides compounds, stereoisomers, tautomers, salts, solvates or prodrugs thereof, wherein the compounds are compounds of Formula I, or they are compounds of Formula Ia:
in ring A, $X^3$, and $X^5$ are CH, and $X^4$ is $CR^3$; and
$R^3$ is selected from the group consisting of H, and $OCH_3$.

In still yet another embodiment, the present invention provides compounds, stereoisomers, tautomers, salts, solvates or prodrugs thereof, wherein the compounds are compounds of Formula I, or they are compounds of Formula Ia:
$R^4$ and $R^5$ are H.

In still yet another embodiment, the present invention provides compounds, stereoisomers, tautomers, salts, solvates or prodrugs thereof, wherein the compounds are compounds of Formula I, or they are compounds of Formula Ia:

(AA)

is selected from the group consisting of phenyl, pyrimidinyl, and thiazolyl; $R^6$ is phenyl, morpholinyl, piperidinyl, all of which may be optionally substituted with one or more $R^b$, $R^c$, $R^d$ and $R^e$;

In still yet another embodiment, the present invention provides compounds, stereoisomers, tautomers, salts, solvates or prodrugs thereof, wherein the compounds are compounds of Formula I, or they are compounds of Formula Ia:
$R^b$, $R^c$, $R^d$ and $R^e$, at each occurrence, are independently selected from OH, (C=O)$NR^{11}R^{12}$, COOH, (C=O)$OR^{14}$,
$R^{11}$ and $R^{12}$ are independently, at each occurrence, selected from the group consisting of H; $C_1$-$C_4$ alkyl, halo-$C_1$-$C_4$-alkyl, and tetrahydrofuranyl; or
$R^{13}$ is independently, at each occurrence, selected from the group consisting of H, and $CH_3$;
$R^{14}$ is independently, at each occurrence, selected from the group consisting of H, and $CH_3$, and
$R^7$ is selected from the group consisting of H, or $CH_3$.

In still yet another embodiment, the present invention provides compounds, stereoisomers, tautomers, salts, solvates or prodrugs thereof, wherein the compounds are compounds of Formula I, or they are compounds of Formula Ia:
$R^b$, $R^c$, $R^d$ and $R^e$, at each occurrence, are independently selected from OH, fluoro, chloro, (C=O)$NR^{11}R^{12}$, COOH, and (C=O)$OR^{14}$;
$R^{11}$ and $R^{12}$ are independently, at each occurrence, selected from the group consisting of H; $C_1$-$C_4$ alkyl, halo-$C_1$-$C_4$-alkyl, hydroxy-$C_1$-$C_4$-alkyl, oxetanyl, and tetrahydrofuranyl; or
$R^{13}$ is independently, at each occurrence, selected from the group consisting of H, and $CH_3$;
$R^{14}$ is independently, at each occurrence, selected from the group consisting of H, and $CH_3$, and
$R^7$ is selected from the group consisting of H, F, or $CH_3$.

In one embodiment, the present invention provides compounds, stereoisomers, tautomers, salts, solvates or prodrugs thereof, wherein the compounds are compounds of Formula I or Ia.

PAR4 compounds of the invention have $IC_{50}$s in the FLIPR Assay (described hereinafter) of about 10 µM, or 5 µM or less, or 500 nM or less, or 10 nM or less. Activity data for Examples 1-4 is described in Example E.

In some embodiments, the present invention provides at least one compound of the present invention or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of a compound of Formula I, or Ia, preferably, a compound selected from one of the examples, more preferably, Examples 1 to 4, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrugs, or estersthereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, or Ia, preferably, a compound selected from one of the examples, more preferably, Examples 1 to 4, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I or Ia, preferably, a compound selected from one of the examples, more preferably, Examples 1 to 4, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, or Ia, preferably, a compound selected from one of the examples, more preferably, Examples 1 to 4, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula Ior Ia, preferably, a compound selected from one of the examples, more preferably, Examples 1 to 4, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, or Ia, preferably, a compound selected from one of the examples, more preferably, Examples 1 to 4, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula Ior Ia, preferably, a compound selected from one of the examples, more preferably, Examples 1 to 4, of the invention.

Other Embodiments of the Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrugs, or estersthereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrugs, or esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials.

All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with at least one halogen, up to fully substituted with halogens (perhaloalkyl), alternatively 1 to 7 halogens or 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

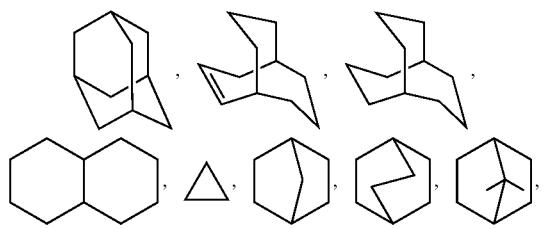

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane).

Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $C_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. The heterocycle may optionally contain a =O. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Heterocyclo groups include

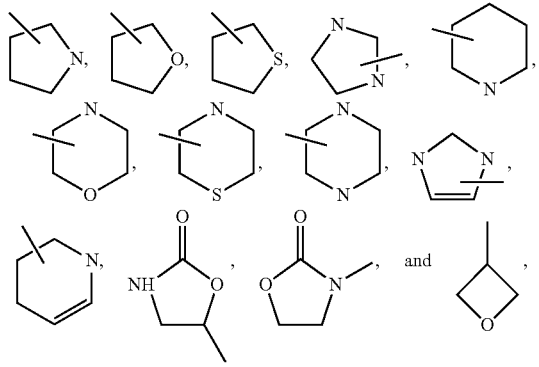

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Heteroaryl groups include, but are not limited to,

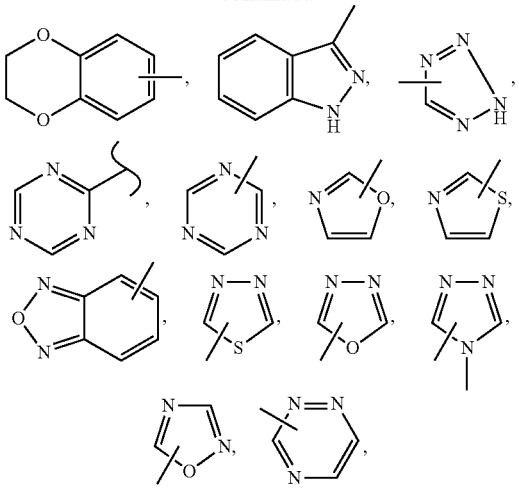

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)R$_e$, as well as the bivalent groups —C(=O)— or —C(=O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "⌇" or "§—" or "—§—" attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et2O | diethyl ether |
| i-PrOH or IPA | isopropanol |
| HOAc | acetic acid |
| BOP reagent | benzotriazol-1-yloxytris(diethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC.HCl) or EDCI (or EDCI.HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperazine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidinophosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTs | tosylate, para-toluenesulfonate |
| PBr$_3$ | phosphorous tribromide |
| Pd(PPh$_3$)$_4$ | tetrakis(triphenylphosphine) palladium (0) |
| (S,S)-EtDuPhosRh(I) | (+)-1,2-bis((2S,5S)-2,5-diethylphospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Compounds of formula 3 of this invention can be obtained by condensation of an amine of formula 1 with a ketone of formula 2 which contains a leaving group X such as a bromide, chloride, iodide or tosylate and a protecting group PG such as benzyl as shown in Scheme 1. Both compounds of formula 1 and 2 are commercially available or can be prepared by means known to one skilled in the art. This condensation is promoted by heating, either thermally or preferably by microwave irradiation. The protecting group can be removed by methods known in the art, such as BCl$_3$ at −78° C. in the presence of pentamethylbenzene. Subsequent alkylation using either an alcohol 4 under Mitsunobu conditions or a bromide 5 in the presence of base such as cesium carbonate provides the compounds of Formula 6. Alcohols 4 and bromides 5 are commercially available or can be prepared by methods known in the art.

Scheme 1

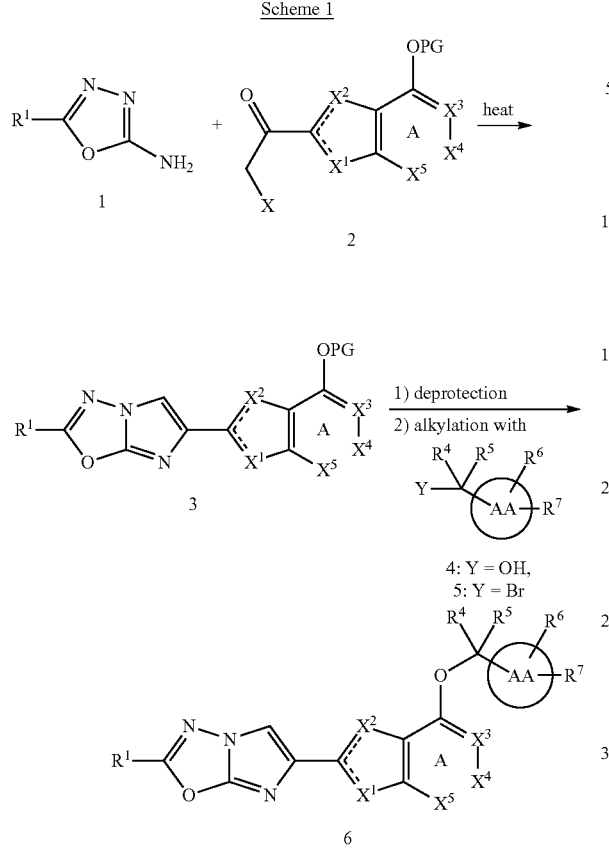

In the event that the condensation of an amine of formula 1 with a ketone of formula 2 does not proceed to compounds of Formula 3 in a single step, compounds of Formula 3 can be prepared from dehydration of compounds of Formula 8 with POCl$_3$, as shown in Scheme 2. Compounds of formula 8 can be prepared from the hydrolysis of compounds of Formula 7, which in turn can be derived from the reaction of an amine of formula 1 with a ketone of formula 2. Compounds 3 can be converted to compounds of Formula 6 by removal of the protecting group (PG) and alkylation as discussed in Scheme 1.

Scheme 2

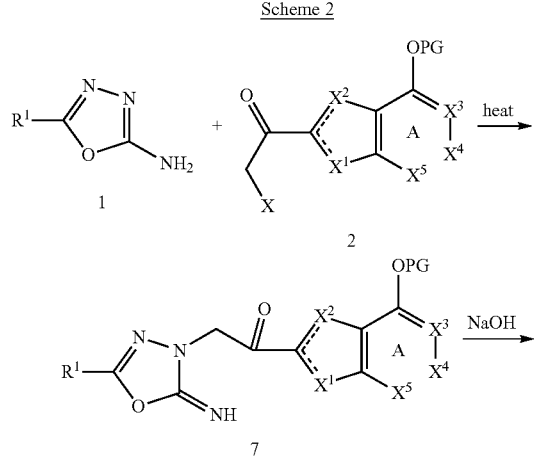

In addition, the PCT publications WO2013/163279, WO2013/163244, and WO2013/163241 disclose synthesis of many reagents of structure 4 and 5 containing ring AA (shown in Schemes 1 and 2) which are useful for preparing compounds of this invention.

Aminooxadiazoles 1 may be commerically available or can be prepared be reacting hydrazides 9 with cyanogen bromide 10, by heating in, for instance, an alcoholic solvent such as methanol, or treating with a base such as sodium bicarbonate or sodium acetate in, for instance, a mixture of water and dioxane. Addition of bromine or iodine may facilitate the reaction.

Scheme 3

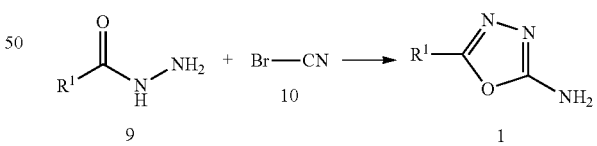

Substituted benzofurans 14, bearing α-bromoketone substituents at the 2-position, can be prepared as shown in Scheme 4. o-Hydroxy benzaldehydes 11 can be prepared by methods known to one skilled in the art of organic synthesis, and can be condensed with ketones of formula 12, bearing a leaving group Q such as chloro, bromo or tosyloxy, to give benzofurans 13. Bromination of compounds of formula 13 affords bromoketones 14, which can be condensed with substituted aminooxadiazoles 1 according to Scheme 1 or 2 to give compounds of Formula I. Bromoketones 14 are a specific subset of compounds 2 in Schemes 1 and 2.

Scheme 4

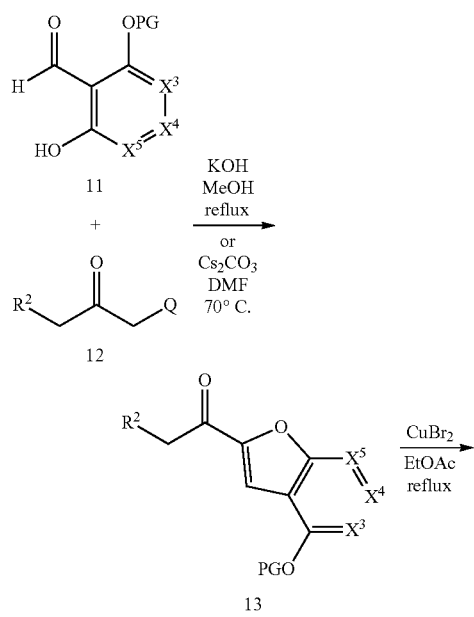

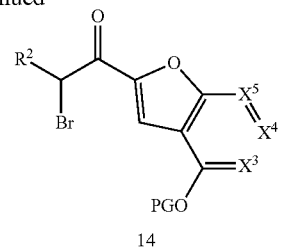

Benzoxazole compounds of Formula I can be prepared starting from substituted aminooxadiazoles 1 and pyruvate esters of formula 15 which contain a leaving group Q such as a bromide, iodide or tosylate as shown in Scheme 5. Both compounds of formula 1 and 14 are commercially available or are available by means known to one skilled in the art. Following condensation and saponification of the esters 16 to form acids 17, amino phenols of formula 18 or 19 are coupled to form amides of formula 20 or 21, which can be cyclized under acid catalysis to form benzoxazole compounds of formula 22 or 23. These can be deprotected and alkylated as shown in Scheme 1 to provide compounds of Formula I.

Scheme 5

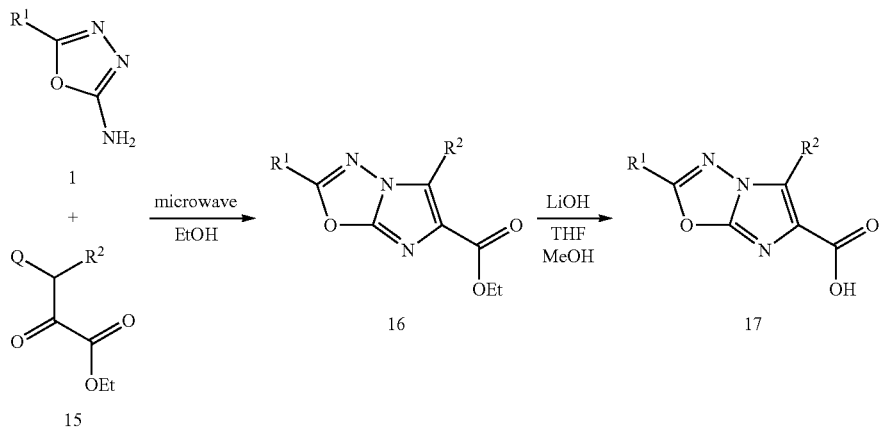

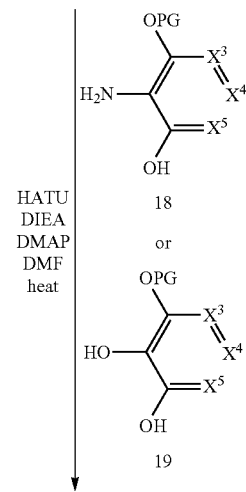

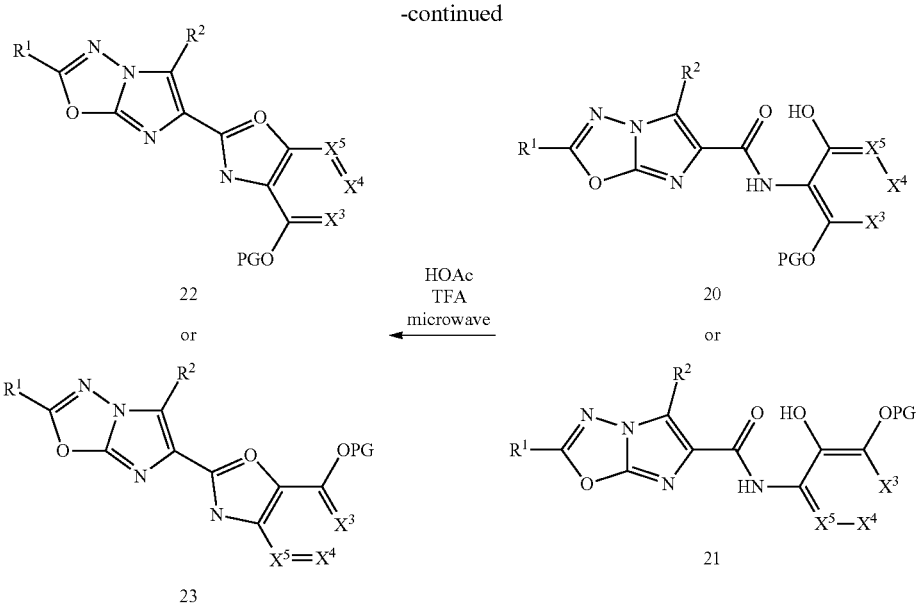

Benzothiazole compounds of the invention can be prepared from intermediates described in Scheme 6. Reaction of bromo anilines 24, which are commercially available or can be prepared by one skilled in the art, with benzoylisothiocyanate affords thioureas 26, which are hydrolyzed with NaOH and heat to afford thioureas 27. These thioureas can be oxidatively cyclized with, for instance, bromine in a solvent such as chloroform, to give aminobenzothiazoles 28. Reaction with an organic nitrite provides benzothiazoles 29. Subsequent deprotonation and reaction with a Weinreb amide gives acylbenzothiazoles 30. These intermediates can be brominated, with for instance, phenyltrimethylammonium tribromide, to give bromoketones 31. These intemediates can be converted to compounds of the invention using chemistry shown in Scheme 1, followed by derivitization of the aryl bromide using methods known to one skilled in the art.

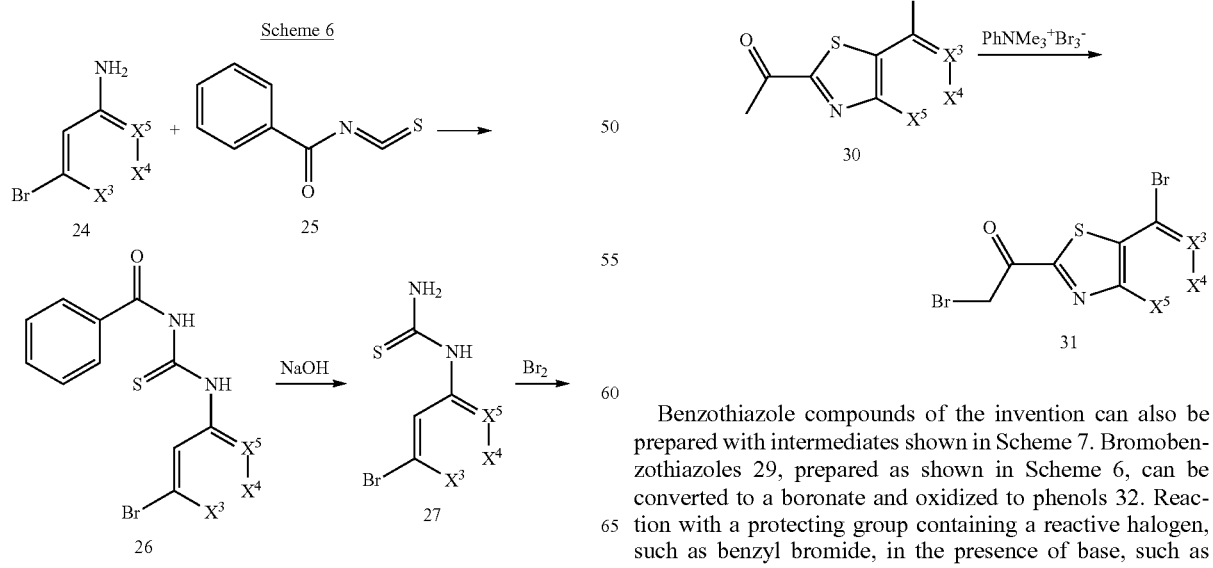

Benzothiazole compounds of the invention can also be prepared with intermediates shown in Scheme 7. Bromobenzothiazoles 29, prepared as shown in Scheme 6, can be converted to a boronate and oxidized to phenols 32. Reaction with a protecting group containing a reactive halogen, such as benzyl bromide, in the presence of base, such as potassium carbonate, affords protected benzothiazoles 33.

Acylation of the benzothiazole 2-position using a Weinreb amide and strong base, and subsequent bromination gives bromoketones 35, which can be converted to compounds of Formula I as shown in Scheme 1.

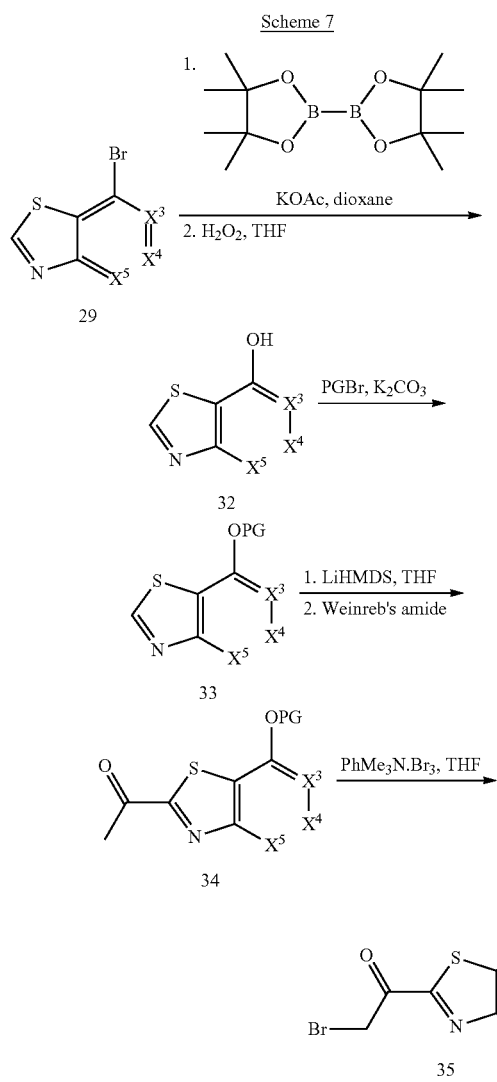

Scheme 7

General Methods

The following methods were used in the exemplified Examples, except where noted otherwise.

Products were analyzed by reverse phase analytical HPLC carried out on a Shimadzu Analytical HPLC system running Discovery VP software using one of the following methods:

Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm).

Method B: PHENOMENEX® Luna C18 column (4.6×50 mm) eluted at 4 mL/min with a 2, 4 or 8 min gradient from 100% A to 100% B (A: 10% acetonitrile, 89.9% water, 0.1% TFA; B: 10% water, 89.9% acetonitrile, 0.1% TFA, UV 220 nm).

Reverse phase preparative HPLC was carried out using a Shimadzu Preparative HPLC system running Discovery VP software using one of the following methods.

Method A: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method B: XBridge C18, 19×200 mm column, 5-am particles; Mobile Phase A: 5:95 acetonitrile: water with 0.1% trifluoroacetic acid; Mobile Phase B: 95:5 acetonitrile: water with 0.1% trifluoroaceticacid; Flow: 20 mL/min.

LCMS chromatograms were obtained on a Shimadzu HPLC system running Discovery VP software, coupled with a Waters ZQ mass spectrometer running MassLynx version 3.5 software using a linear gradient using solvent A (10% acetonitrile, 90% water, 0.1% of TFA) and solvent B (90% acetonitrile, 10% water, 0.1% of TFA); Column: BEH C18 2.1×50 mm; wavelength 220 nm; flow rate 0.8 mL/min; gradient time 1.5 min; 2 to 98% B.

In addition, the following orthogonal HPLC conditions were used to check the purity of the compounds:

Method A: Two analytical LC/MS injections were used to determine the final purity. Injectionl condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. and UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. and UV detection was set to 220 nm. The LC column was maintained at room temperature.

Method B: Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

EXAMPLES

The following Examples have been prepared, isolated and characterized using the methods disclosed herein. The following examples are not meant to be limiting of the scope of the invention.

Example 1

6-(4-(benzyloxy)-6-methoxybenzofuran-2-yl)-2-ethylimidazo[2,1-b][1,3,4]oxadiazole

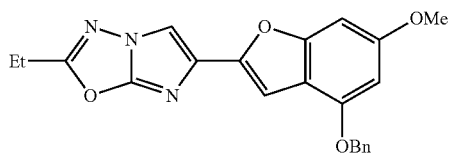 [SMILES: CCc1nn2cc(-c3cc4c(OCc5ccccc5)cc(OC)cc4o3)nc2o1]

Example 1A 1-(4-(benzyloxy)-6-methoxybenzofuran-2-yl)-2-(5-ethyl-2-imino-1,3,4-oxadiazol-3(2H)-yl)ethanone hydrobromide

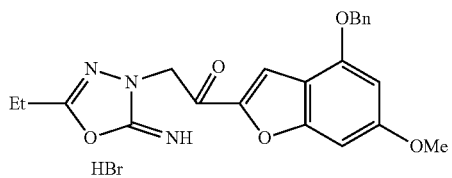 [SMILES: CCc1nn(CC(=O)c2cc3c(OCc4ccccc4)cc(OC)cc3o2)c(=N)o1 ; Br]

A suspension of 5-ethyl-1,3,4-oxadiazol-2-amine (139 mg, 1.231 mmol) and 1-(4-(benzyloxy)-6-methoxybenzofuran-2-yl)-2-bromoethanone (385 mg, 1.026 mmol, for preparation, see PCT Int. Appl. (2013), WO 2013163241) in isopropanol (6 mL) was heated in a sealed vial at 75° C. The suspension turned to a clear solution. The reaction mixture was kept stirring at 75° C. overnight. Precipitate formed at the end of the reaction. The reaction mixture was triturated with diethyl ether. The precipitate was collected by filtration, washed with diethyl ether and dried under vacuum to give Example 1A (404 mg, 0.827 mmol, 81% yield) as a white solid. $^1$H NMR (400 MHz, DMSO-$d_6$) δ 8.25 (s, 1H), 7.58-7.52 (m, 2H), 7.48-7.43 (m, 2H), 7.41-7.37 (m, 1H), 6.99 (s, 1H), 6.67 (d, J=1.8 Hz, 1H), 5.67 (s, 2H), 5.31 (s, 2H), 3.87 (s, 3H), 2.88 (q, J=7.5 Hz, 2H), 1.24 (t, J=7.5 Hz, 3H); LC-MS: RT=0.75 min, MS (ESI) m/z: 408.1 (M+H)

Example 1B

N-(4-(4-(benzyloxy)-6-methoxybenzofuran-2-yl)-2-oxo-2,3-dihydro-1H-imidazol-1-yl)propionamide

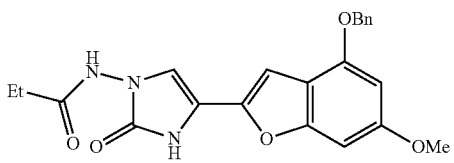 [SMILES: CCC(=O)Nn1cc(-c2cc3c(OCc4ccccc4)cc(OC)cc3o2)[nH]c1=O]

To a solution of Example 1A (404 mg, 0.827 mmol) in water (6 mL) and THF (3 mL) was added 1.0 N NaOH (1.075 mL, 1.075 mmol). The reaction mixture was heated at 60° C. for 2.0 h. LCMS indicated a clean reaction. The reaction mixture was diluted with EtOAc/0.5 N HCl. The organic layer was washed with brine, dried over sodium sulfate and concentrated to give Example 1B (337 mg, 0.827 mmol, 100% yield) as a brown solid. It was used for the next step without further purification. $^1$H NMR (400 MHz, DMSO-$d_6$) δ 10.91 (d, J=2.0 Hz, 1H), 10.61 (s, 1H), 7.51 (d, J=6.8 Hz, 2H), 7.47-7.41 (m, 2H), 7.40-7.34 (m, 1H), 6.98-6.93 (m, 2H), 6.78 (d, J=0.9 Hz, 1H), 6.54 (d, J=2.0 Hz, 1H), 5.23 (s, 2H), 3.79 (s, 3H), 2.25 (q, J=7.6 Hz, 2H), 1.11-1.05 (m, 3H); LC-MS: RT=0.79 min, MS (ESI) m/z: 408.1 (M+H)$^+$

Example 1

Example 1B (50 mg, 0.123 mmol) in POCl$_3$ (0.5 mL) was heated at 105° C. under Argon for 45 min. After the reaction mixture was cooled to rt, it was diluted with EtOAc, quenched with cold water. The organic layer was washed with 1.5 M dipotassium phosphate, brine, dried over sodium sulfate and concentrated. The crude residue was purified using a preparative HPLC (method A, 70-100% B in 10 mins; RT=6.0 min). The desired fractions were placed in a speedvac overnight to remove solvent, then lyophilized to give Example 1 (5.0 mg, 0.012 mmol, 9.63% yield) as a slightly brown lyophilate. $^1$H NMR (400 MHz, chloroform-d) δ 7.54-7.45 (m, 3H), 7.40 (t, J=7.4 Hz, 2H), 7.34 (d, J=7.0 Hz, 1H), 7.11 (s, 1H), 6.68 (s, 1H), 6.40 (d, J=1.3 Hz, 1H), 5.18 (s, 2H), 3.83 (s, 3H), 2.92 (q, J=7.6 Hz, 2H), 1.43 (t, J=7.5 Hz, 3H). LC-MS: RT=1.15 min, MS (ESI) m/z: 390.4 (M+H)$^+$ Analytical HPLC purity (method A): 93%.

Example 2

4-(4-(((2-(2-ethylimidazo[2,1-b][1,3,4]oxadiazol-6-yl)-6-methoxybenzofuran-4-yl)oxy)methyl)thiazol-2-yl)-N,N-dimethylbenzamide

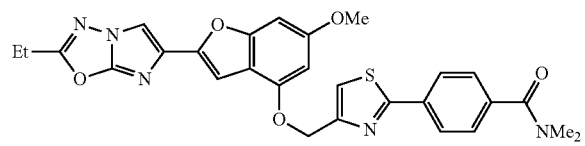 [SMILES: CCc1nn2cc(-c3cc4c(OCc5csc(-c6ccc(C(=O)N(C)C)cc6)n5)cc(OC)cc4o3)nc2o1]

Example 2A 2-(2-ethylimidazo[2,1-b][1,3,4]oxadiazol-6-yl)-6-methoxybenzofuran-4-ol

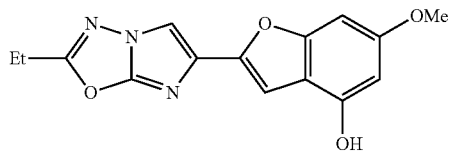 [SMILES: CCc1nn2cc(-c3cc4c(O)cc(OC)cc4o3)nc2o1]

Example 1

40 mg, 0.103 mmol) and pentamethylbenzene (107 mg, 0.719 mmol) were dissolved in dichloromethane (2.0 mL)

and cooled to −78° C. 1.0 M boron trichloride in heptane (0.267 mL, 0.267 mmol) was added. The reaction mixture was stirred at −78° C. for 40 min, and at rt for 40 min. The reaction mixture was diluted with EtOAc, quenched with 0.5 N HCl and extracted with EtOAc (3×). The combined organic layers were washed with brine, dried over sodium sulfate and concentrated. The crude product was purified by flash chromatography (loading in chloroform/MeOH, 10% to 100% EtOAc in hexanes over 10 min using a 4 g silica gel cartridge). The desired fractions were combined and concentrated to yield Example 2A (23 mg, 0.077 mmol, 74.8% yield) as a pale yellow solid. $^1$H NMR (400 MHz, methanol-$d_4$) δ 7.57 (s, 1H), 7.03 (s, 1H), 6.61 (dd, J=2.0, 0.9 Hz, 1H), 6.32 (d, J=2.0 Hz, 1H), 3.84-3.82 (s, 3H), 2.96 (q, J=7.6 Hz, 2H), 1.27 (t, J=7.2 Hz, 3H); LC-MS: RT=0.76 min, MS (ESI) m/z: 300.0 (M+H)$^+$.

Example 2B 4-(4-(Bromomethyl)thiazol-2-yl)-N,N-dimethylbenzamide

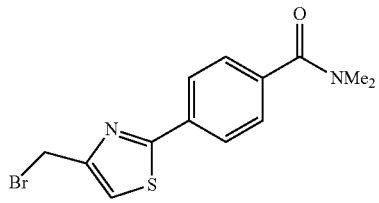 [SMILES: CN(C)C(=O)c1ccc(-c2nc(CBr)cs2)cc1]

To an ice-cold mixture of 4-(4-(hydroxymethyl)thiazol-2-yl)-N,N-dimethylbenzamide (0.525 g, 2.000 mmol, for preparation, see PCT Int. Appl. (2013), WO 2013163279) in DCM (15 mL) under N$_2$ was added phosphorous tribromide (0.095 mL, 1.000 mmol) dropwise. After 5 min the cooling bath was removed and the mixture was stirred at room temperature for 3 h, at which time LCMS showed that no starting material remained. The resulting white suspension was poured into a mixture of ice (50 mL) and saturated aqueous NaHCO$_3$ (50 mL) and extracted with DCM (2×100 mL). The combined organic phase was washed (brine), dried (Na$_2$SO$_4$) and evaporated to give a pale yellow gum. Flash chromatography (Isco/50-100% EtOAc-DCM; rapid elution on a 24 g column) afforded Example 2B (0.549 g, 84% yield) as a colorless gum which solidified on standing in vacuo to give a white solid. This material was used as such in the next step. $^1$HNMR (400 MHz, DMSO-$d_6$) δ 7.98 (d, J=8.6 Hz, 2H), 7.87 (s, 1H), 7.53 (d, J=8.2 Hz, 2H), 4.81 (s, 2H), 2.99 (br s, 3H), 2.92 (br s, 3H). HRMS (ESI): Calcd. for C$_{13}$H$_{14}$BrN$_2$OS [M+H]+m/z 325.0010. found 325.0003.

Example 2

To Example 2A (23 mg, 0.077 mmol) in DMF (2.0 mL) at rt was added cesium carbonate (43.8 mg, 0.134 mmol). The mixture was stirred at rt for 10 min, followed by addition of Example 2B (27.5 mg, 0.085 mmol). The reaction mixture was stirred at rt for 30 min. It was diluted with EtOAc, washed with water, brine, dried over sodium sulfate and concentrated. The crude was dissolved in DMSO and purified via preparative LC/MS (method B, 20-75% B over 20 min, then a 5-min hold at 100% B). Fractions containing the desired product were combined and dried via centrifugal evaporation to yield Example 2 (26.6 mg, 0.046 mmol, 59.9% yield). $^1$H NMR (500 MHz, DMSO-$d_6$) δ 8.06-7.90 (m, 4H), 7.53 (d, J=7.9 Hz, 2H), 7.02 (s, 1H), 6.84 (s, 1H), 6.64 (s, 1H), 5.38 (s, 2H), 3.82 (s, 3H), 3.40-3.35 (m, 1H), 3.04-2.86 (m, 7H), 1.30 (t, J=7.3 Hz, 3H); LC-MS: RT=2.05 min, MS (ESI) m/z: 544.2 (M+H)$^+$. Analytical HPLC purity (method B): 94%.

Example 3

6-(4-(benzyloxy)-6-methoxybenzofuran-2-yl)-2-methylimidazo[2,1-b][1,3,4]oxadiazole

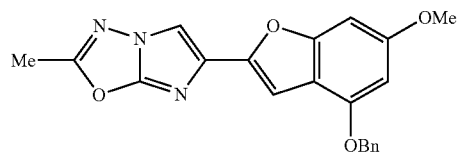 [SMILES: COc1cc(OCc2ccccc2)c2cc(-c3cn4nc(C)oc4n3)oc2c1]

Example 3A 1-(4-(benzyloxy)-6-methoxybenzofuran-2-yl)-2-(2-imino-5-methyl-1,3,4-oxadiazol-3(2H)-yl)ethanone hydrobromide

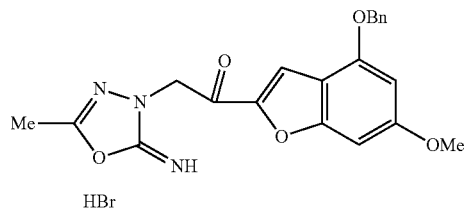 [SMILES: COc1cc(OCc2ccccc2)c2cc(C(=O)Cn3nc(C)oc3=N)oc2c1 ; Br]

A suspension of 5-methyl-1,3,4-oxadiazol-2-amine (206 mg, 2.083 mmol) and 1-(4-(benzyloxy)-6-methoxybenzofuran-2-yl)-2-bromoethanone (521 mg, 1.389 mmol, for preparation, see PCT Int. Appl. (2013), WO 2013163241) in isopropanol (12 mL) was heated in a sealed vial at 78° C. The suspension turned to a clear solution. The reaction mixture was kept stirring at 78° C. overnight. Precipitate formed at the end of the reaction. The reaction mixture was triturated with diethyl ether. The precipitate was collected by filtration, washed with diethyl ether and dried under vacuum to give Example 3A (570 mg, 1.202 mmol, 87% yield). $^1$H NMR (500 MHz, DMSO-$d_6$) δ 8.23 (s, 1H), 7.54 (d, J=7.2 Hz, 2H), 7.44 (t, J=7.4 Hz, 2H), 7.39 (d, J=7.4 Hz, 1H), 6.98 (s, 1H), 6.67 (d, J=1.7 Hz, 1H), 5.65 (s, 2H), 5.30 (s, 2H), 3.86 (s, 3H), 2.51 (s, 3H). LC-MS: RT=0.90 min, MS (ESI) m/z: 394.05 (M+H)$^+$

Example 3B

N-(4-(4-(benzyloxy)-6-methoxybenzofuran-2-yl)-2-oxo-2,3-dihydro-1H-imidazol-1-yl)acetamide

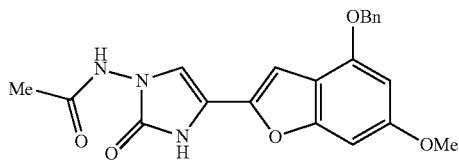 [SMILES: COc1cc(OCc2ccccc2)c2cc(-c3cn(NC(C)=O)c(=O)[nH]3)oc2c1]

To a suspension of Example 3A (630 mg, 1.328 mmol) in water (12 mL) and THF (10 mL) was added 1.0 N NaOH (1.727 mL, 1.727 mmol). The reaction mixture turned clear and was heated at 60° C. for 2.5 h. LCMS indicated a clean reaction. The reaction mixture was diluted with EtOAc and the pH was adjusted to 4-5 with 0.5 N HCl. The organic layer was washed with brine, dried over sodium sulfate and concentrated to give Example 3B (447 mg, 1.136 mmol, 86% yield) as a brown solid. It was used for the next step without further purification. $^1$H NMR (400 MHz, chloroform-d) δ 7.41-7.23 (m, 5H), 6.70 (br. s., 1H), 6.47 (br. s., 1H), 6.36 (br. s., 1H), 6.23 (br. s., 1H), 5.02 (br. s., 2H), 3.66 (s, 3H), 2.04 (s, 3H). LC-MS: RT=0.953 min, MS (ESI) m/z: 394.05 (M+H)+$^+$.

Example 3

Example 3B (50 mg, 0.127 mmol) in POCl$_3$ (0.5 mL) was heated at 105° C. under Argon for 45 min. After the reaction mixture was cooled to rt, it was diluted with EtOAc, quenched with cold water. The organic layer was washed with 1.5 M dipotassium phosphate, brine, dried over sodium sulfate and concentrated. The crude product was purified by flash chromatography (loading in chloroform, 0% to 45% EtOAc in hexanes over 10 min using a 4 g silica gel cartridge). The desired fractions were combined and concentrated to yield a crude product (12 mg). The crude product was dissolved in DMSO and purified via preparative LC/MS (method B, 25-100% B over 20 min, then a 5-min hold at 100% B). Fractions containing the desired product were combined and dried via centrifugal evaporation to yield Example 3 (7.8 mg, 0.021 mmol, 16% yield) as a white solid. $^1$H NMR (500 MHz, DMSO-d$_6$) δ 8.00 (s, 1H), 7.50 (d, J=7.0 Hz, 2H), 7.41 (t, J=7.2 Hz, 2H), 7.34 (d, J=6.7 Hz, 1H), 6.95 (s, 1H), 6.81 (br. s., 1H), 6.51 (br. s., 1H), 5.24 (s, 2H), 3.77 (s, 3H), 2.58 (s, 3H). LC-MS: RT=2.1 min, MS (ESI) m/z: 376.1 (M+H)$^+$. Analytical HPLC purity (method B): 100%.

Example 4

4-(4-(((6-methoxy-2-(2-methylimidazo[2,1-b][1,3,4]oxadiazol-6-yl)benzofuran-4-yl)oxy)methyl)thiazol-2-yl)-N,N-dimethylbenzamide

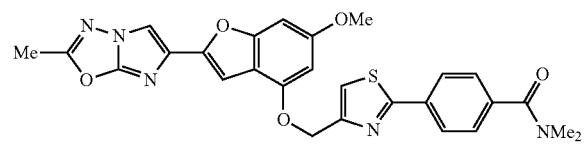

Example 4A 6-methoxy-2-(2-methylimidazo[2,1-b][1,3,4]oxadiazol-6-yl)benzofuran-4-ol

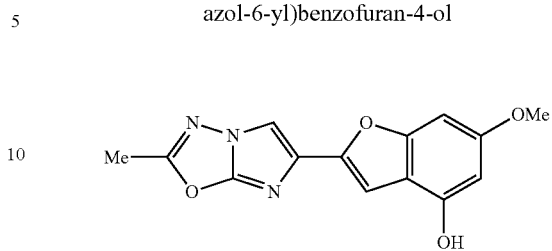

Example 3

(30 mg, 0.080 mmol) and pentamethylbenzene (83 mg, 0.559 mmol) were dissolved in dichlooromethane (2.0 mL) and cooled to −78° C. 1.0 M boron trichloride in heptane (0.208 mL, 0.208 mmol) was added. The reaction mixture was stirred at −78° C. for 40 min, and at rt for 40 min. The reaction mixture was diluted with EtOAc, quenched with 0.5 N HCl and extracted thrice with EtOAc. The combined organic layers were washed with brine, dried over sodium sulfate and concentrated. The crude product was purified by flash chromatography (loading in chloroform/MeOH, 5% to 100% EtOAc in dichloromethane over 10 min using a 4 g silica gel cartridge). The desired fractions were combined and concentrated to yield Example 4A (10 mg, 0.035 mmol, 43.9% yield) as a pale yellow solid. $^1$H NMR (400 MHz, methanol-d$_4$) δ 7.48 (s, 1H), 6.93 (s, 1H), 6.51 (d, J=1.1 Hz, 1H), 6.22 (d, J=2.0 Hz, 1H), 3.73 (s, 3H), 2.54 (s, 3H). LC-MS: RT=0.70 min, MS (ESI) m/z: 286.0 (M+H)$^+$,

Example 4

Example 4A (20 mg, 0.070 mmol) and 4-(4-(hydroxymethyl)thiazol-2-yl)-N,N-dimethylbenzamide (20.23 mg, 0.077 mmol, for preparation, see PCT Int. Appl. (2013), WO 2013163279) were placed in a flask and vacuumed for 15 min. The flask was backfilled with nitrogen and dry THF (995 μl) was added. tri-n-Butylphosphine (43.2 μl, 0.175 mmol) was added in one portion. A solution of 1,1'-(azodicarbonyl) dipiperidine (44.2 mg, 0.175 mmol) in dry THF (497 μl) was added. The reaction mixture was stirred at rt overnight, diluted with EtOAc, washed with 0.5 N HCl, brine and dried over sodium sulfate. After evaporation of solvent, the crude residue was purified using a preparative HPLC (method A, 45-100% B in 10 min. RT=4.2 min). The desired fractions were placed in a speedvac over night to remove solvent, then lyophilized to give Example 4 (11.4 mg, 0.020 mmol, 29.2% yield) as a white lyophilate. $^1$H NMR (400 MHz, chloroform-d) δ 8.04-7.99 (m, 2H), 7.55-7.49 (m, 3H), 7.42 (s, 1H), 7.14 (s, 1H), 6.72-6.69 (m, 1H), 6.46 (d, J=2.0 Hz, 1H), 5.39 (d, J=0.7 Hz, 2H), 3.85 (s, 3H), 3.14 (s, 3H), 3.02 (s, 3H), 2.62 (s, 3H); LC-MS: RT=0.858 min, MS (ESI) m/z: 530.1 (M+H)$^+$, Analytical HPLC purity (method B): 95%.

In a similar manner, the following compounds could be prepared:

| Compound | Structure |
|---|---|
| 5 | 2-ethyl-imidazo[2,1-b][1,3,4]oxadiazole linked to 6-methoxy-benzofuran-4-yloxymethyl-(2-phenyl-thiazol-4-yl) |
| 6 | 2-ethyl-imidazo[2,1-b][1,3,4]oxadiazole linked to 6-methoxy-benzofuran-4-yloxymethyl-(5-methyl-2-morpholino-thiazol-4-yl) |
| 7 | 2-ethyl-imidazo[2,1-b][1,3,4]oxadiazole linked to 6-methoxy-benzofuran-4-yloxymethyl-(2-(tetrahydro-2H-pyran-4-yl)-thiazol-4-yl) |
| 8 | 2-ethyl-imidazo[2,1-b][1,3,4]oxadiazole linked to 6-methoxy-benzofuran-4-yloxymethyl-(2-(4,4-difluorocyclohexyl)-thiazol-4-yl) |
| 9 | 2-ethyl-imidazo[2,1-b][1,3,4]oxadiazole linked to 6-methoxy-benzofuran-4-yloxymethyl-(2-(4-hydroxy-tetrahydro-2H-pyran-4-yl)-thiazol-4-yl) |
| 10 | 2-ethyl-imidazo[2,1-b][1,3,4]oxadiazole linked to 6-methoxy-benzoxazol-4-yloxymethyl-(2-phenyl-thiazol-4-yl) |
| 11 | 2-ethyl-imidazo[2,1-b][1,3,4]oxadiazole linked to 5-methoxy-benzoxazol-7-yloxymethyl-(2-phenyl-thiazol-4-yl) |
| 12 | 2-ethyl-imidazo[2,1-b][1,3,4]oxadiazole linked to 5-methoxy-benzothiazol-7-yloxymethyl-(2-phenyl-thiazol-4-yl) |

-continued

| Compound | Structure |
|---|---|
| 13 | 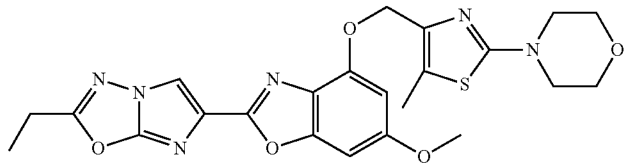 [SMILES: CCc1nn2cc(-c3nc4c(OCc5nc(N6CCOCC6)sc5C)cc(OC)cc4o3)nc2o1] |
| 14 | 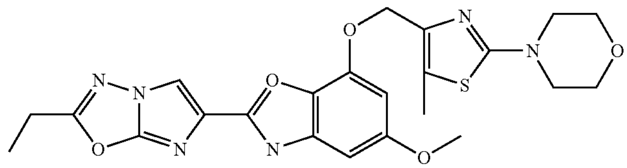 |
| 15 | 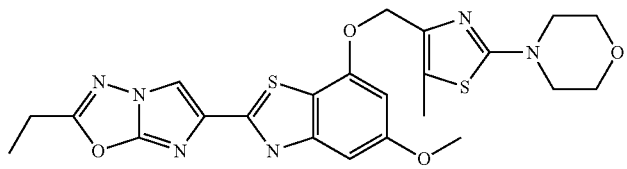 |
| 16 | 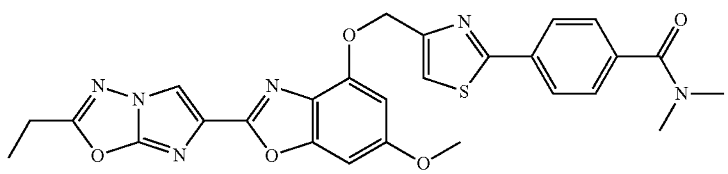 [SMILES: CCc1nn2cc(-c3nc4c(OCc5csc(-c6ccc(C(=O)N(C)C)cc6)n5)cc(OC)cc4o3)nc2o1] |
| 17 | 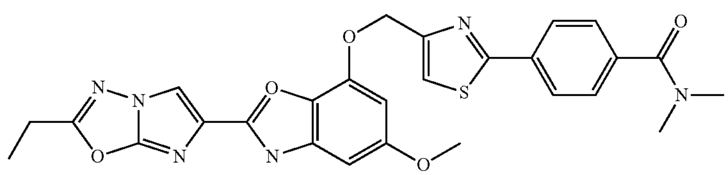 |
| 18 | 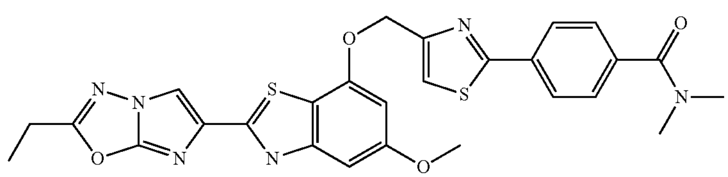 |
| 19 | 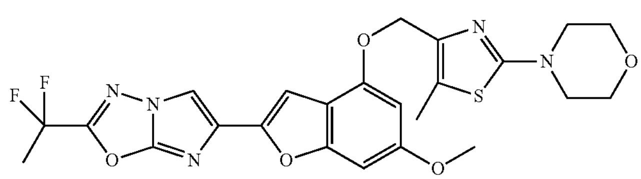 [SMILES: COc1cc(OCc2nc(N3CCOCC3)sc2C)c2cc(-c3cn4nc(C(C)(F)F)oc4n3)oc2c1] |
| 20 | 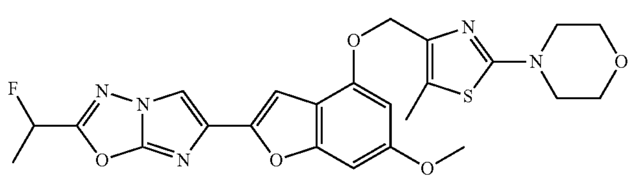 [SMILES: COc1cc(OCc2nc(N3CCOCC3)sc2C)c2cc(-c3cn4nc(C(C)F)oc4n3)oc2c1] |
| 21 | 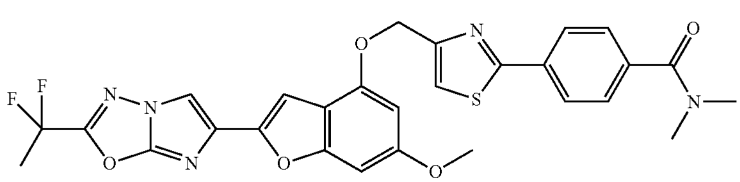 [SMILES: COc1cc(OCc2csc(-c3ccc(C(=O)N(C)C)cc3)n2)c2cc(-c3cn4nc(C(C)(F)F)oc4n3)oc2c1] |

| Compound | Structure |
|---|---|
| 22 | 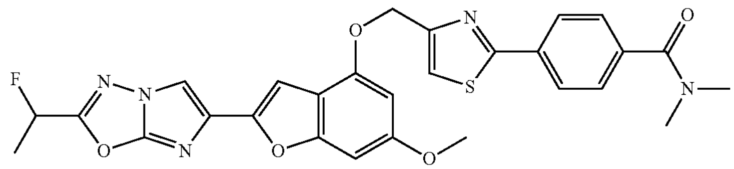 [SMILES: COc1cc(OCc2csc(-c3ccc(C(=O)N(C)C)cc3)n2)c2cc(-c3cn4nc(C(C)F)oc4n3)oc2c1] |
| 23 | 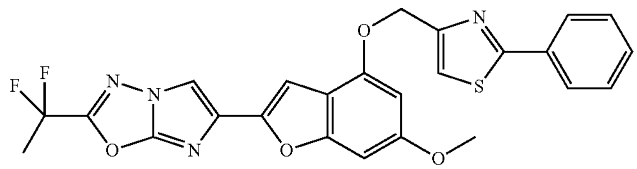 [SMILES: COc1cc(OCc2csc(-c3ccccc3)n2)c2cc(-c3cn4nc(C(C)(F)F)oc4n3)oc2c1] |
| 24 | 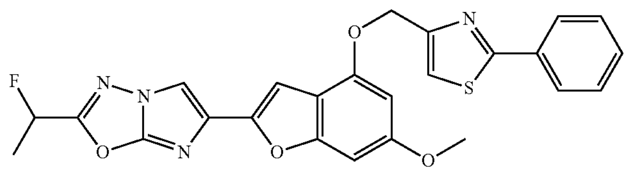 [SMILES: COc1cc(OCc2csc(-c3ccccc3)n2)c2cc(-c3cn4nc(C(C)F)oc4n3)oc2c1] |
| 25 | 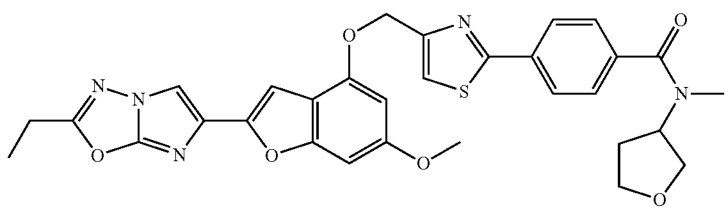 [SMILES: CCc1nn2cc(-c3cc4c(OCc5csc(-c6ccc(C(=O)N(C)C7CCOC7)cc6)n5)cc(OC)cc4o3)nc2o1] |
| 26 | 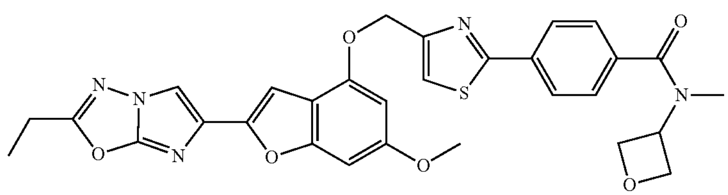 [SMILES: CCc1nn2cc(-c3cc4c(OCc5csc(-c6ccc(C(=O)N(C)C7COC7)cc6)n5)cc(OC)cc4o3)nc2o1] |
| 27 | 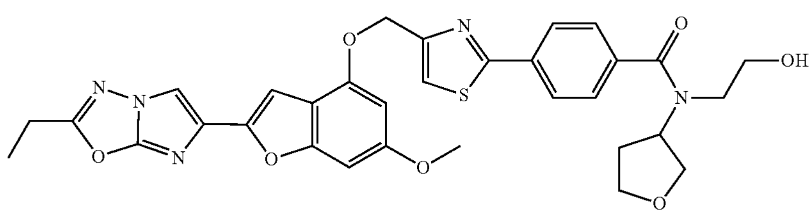 [SMILES: CCc1nn2cc(-c3cc4c(OCc5csc(-c6ccc(C(=O)N(CCO)C7CCOC7)cc6)n5)cc(OC)cc4o3)nc2o1] |
| 28 | 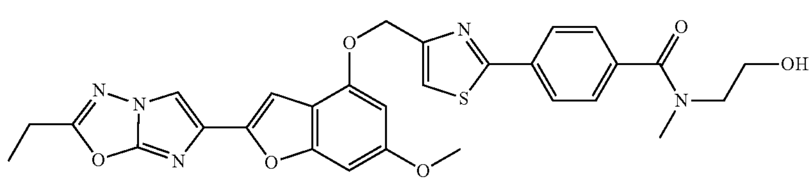 [SMILES: CCc1nn2cc(-c3cc4c(OCc5csc(-c6ccc(C(=O)N(C)CCO)cc6)n5)cc(OC)cc4o3)nc2o1] |
| 29 | 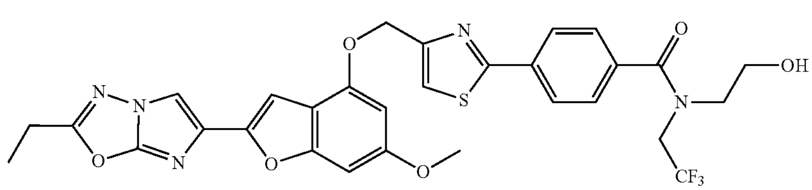 [SMILES: CCc1nn2cc(-c3cc4c(OCc5csc(-c6ccc(C(=O)N(CCO)CC(F)(F)F)cc6)n5)cc(OC)cc4o3)nc2o1] |

-continued

| Compound | Structure |
|---|---|
| 30 | 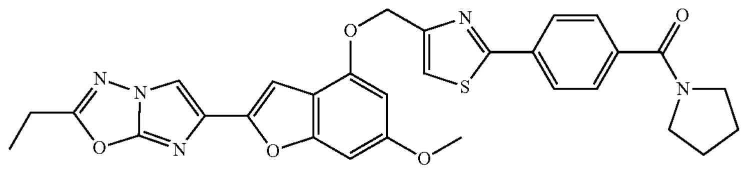 [SMILES: CCc1nn2cc(-c3cc4c(OCc5csc(-c6ccc(C(=O)N7CCCC7)cc6)n5)cc(OC)cc4o3)nc2o1] |
| 31 | 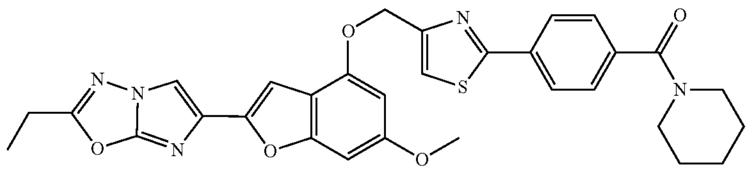 [SMILES: CCc1nn2cc(-c3cc4c(OCc5csc(-c6ccc(C(=O)N7CCCCC7)cc6)n5)cc(OC)cc4o3)nc2o1] |
| 32 | 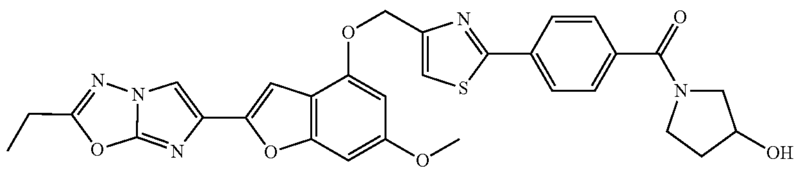 [SMILES: CCc1nn2cc(-c3cc4c(OCc5csc(-c6ccc(C(=O)N7CCC(O)C7)cc6)n5)cc(OC)cc4o3)nc2o1] |
| 33 | 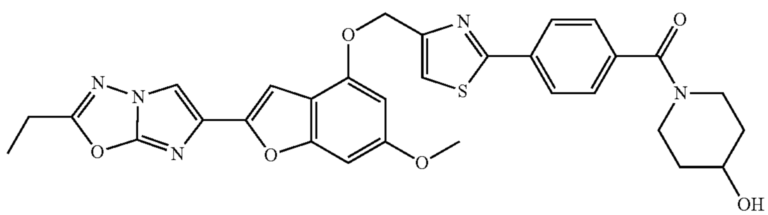 [SMILES: CCc1nn2cc(-c3cc4c(OCc5csc(-c6ccc(C(=O)N7CCC(O)CC7)cc6)n5)cc(OC)cc4o3)nc2o1] |
| 34 | 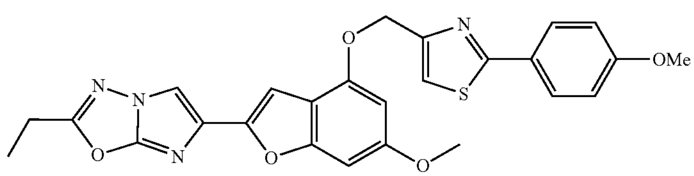 [SMILES: CCc1nn2cc(-c3cc4c(OCc5csc(-c6ccc(OC)cc6)n5)cc(OC)cc4o3)nc2o1] |
| 35 | 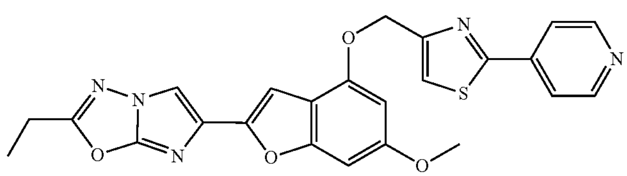 [SMILES: CCc1nn2cc(-c3cc4c(OCc5csc(-c6ccncc6)n5)cc(OC)cc4o3)nc2o1] |
| 36 | 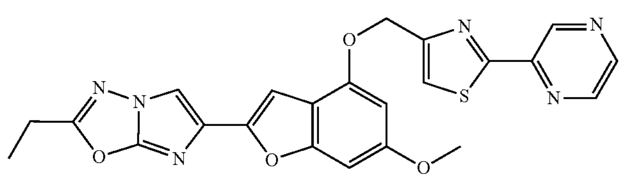 [SMILES: CCc1nn2cc(-c3cc4c(OCc5csc(-c6cnccn6)n5)cc(OC)cc4o3)nc2o1] |
| 37 | 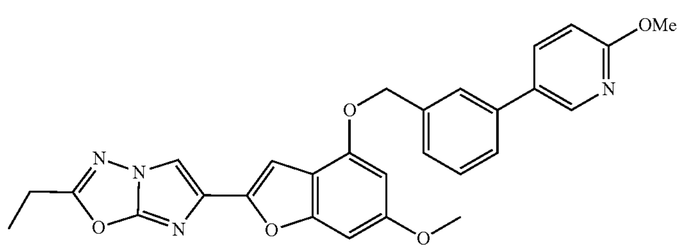 [SMILES: CCc1nn2cc(-c3cc4c(OCc5cccc(-c6ccc(OC)nc6)c5)cc(OC)cc4o3)nc2o1] |

| Compound | Structure |
|---|---|
| 38 | (chemical structure) |
| 39 | (chemical structure) |
| 40 | (chemical structure) |

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid *communis*, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts.

They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, or Ia, preferably, a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-NH$_2$. H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example B. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example C is an alpha-thrombin-induced platelet aggregation assay. Alpha-thrombin activates both PAR1 and PAR4. The ability of a compounds of the present invention to inhibit platelet aggregation may be measured using a standard optical aggregometer. Example D is a tissue factor-induced platelet aggregation assay. The conditions in this assay mimic the physiological events during thrombus formation. In this assay, platelet aggregation in human PRP was initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example F describes an in vivo model of arterial thrombosis in cynomolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay (EC$_{50}$ value of 8 M for H-Ala-Phe(4-F)-Pro-Gly-Trp-Leu-Val-Lys-Asn-Gly-NH$_2$ and 60 M for AYPGKF) and in washed platelet aggregation assay (EC$_{50}$ value of 0.9 M for H-Ala-Phe(4-F)-Pro-Gly-Trp-Leu-Val-Lys-Asn-Gly-NH$_2$ and 12 μM for AYPGKF).

2) PAR4 Expressing Cells

HEK293 cells stably expressing PAR4 were generated by a standard method of transfection of human PAR4 (F2R$^{23}$) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl$_2$, 1 mM CaCl$_2$, 5 mM glucose, 20 mM HEPES pH 7.4).

Example A

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 10% heat-inactivated FBS, 1% Penicillin-Streptomycin, 10 µg/mL blasticidin, and 100 µg/mL Zeocin at 37° C. with 5% CO$_2$. Cells were plated overnight prior to the experiment in a black 384-well Purecoat Amine clear bottom plate (Becton Dickinson Biosciences, San Jose, Calif.) at 10,000 cells/well in 30 µL growth medium and incubated in a humidified chamber at 37° C. with 5% CO$_2$ overnight. Prior to compound addition, the cell medium was replaced with 40 µL of 1X calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C. and a further 30 minute incubation and equilibration period at room temperature, 20 µL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 µL of agonist peptide for antagonist activity measurement. The PAR4 agonist peptide (H-Ala-Phe(4-F)-Pro-Gly-Trp-Leu-Val-Lys-Asn-Gly-NH$_2$) and the PAR1 agonist peptide (SFFLRR) were routinely tested to ensure a proper response at the EC$_{50}$ value in the assay (~5 µM for PAR4 agonist peptide and ~2 µM for PAR1 agonist peptide). Compound potency was derived from 11-point concentration-response curves.

Example B

Gamma Thrombin Induced Platelet Aggregation Assays

The ability of the compound(s) of the current invention to inhibit platelet aggregation induced by gamma-thrombin was tested in a 96-well microplate aggregation assay format. Briefly, 90 µL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 µL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100−100*[ODcompound−ODminimum]/[ODmaximum−ODminimum]). The IC$_{50}$ value of the test compound was calculated by fitting the % IPA values to the one-site concentration response equation: Y=A+(B−A)/{1+(C/X)^D]}, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example C

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 µl of washed platelets at stirring speed of 1000 rpm. Platelet aggregation is monitored using an Optical Aggregometer (Chrono-Log, Havertown, Pa.) and the area under the curve (AUC) at 6 min was measured. IC$_{50}$ values are calculated using vehicle control as 0% inhibition.

Example D

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example E

As indicated above, the FLIPR assay, an in vitro assay, measures the PAR4 antagonist activity of compounds tested as described in Example A. Examples 1-4 have been tested in the PAR4 FLIPR assay and have been found to have an $EC_{50}$<5 µM.

Example F

Cynomolgus Monkey Electrolytic Injury-induced Carotid Artery Thrombosis Model

Healthy cynomolgus monkeys can be used in the study. These monkeys are retired from other pharmacokinetic and pharmacodynamic studies and had at least a 4-week washout period.

On the day of the study, compounds or vehicles are administered orally at 1 to 2 hours before the experiment. Monkeys are then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs.

The carotid arterial thrombosis model in monkeys is based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295:212-218 (2002).) Thrombosis is induced by electrical stimulation of the carotid artery for 5 min at 10 mA using an external stainless-steel bipolar electrode. Carotid blood flow is measured with an appropriately sized TRANSONIC® flow probe and a TRANSONIC® perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow had been maintained continuously for 90 min. In addition, thrombus from the injured artery is removed, blotted twice on a weighing paper to remove residual fluid, and weighed.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

I or a stereoisomer, tautomer, pharmaceutically acceptable salt, solvate or prodrug thereof, wherein:

the dashed line represents an optional double-bond $X^1$ is O and $X^2$ is CH, $CR^{10}$, or N; or $X^1$ is N and $X^2$ is O; or $X^1$ is N, CH, or $CR^{10}$, and $X^2$ is S; or $X^1$ is N and $X^2$ is NH; or $X^1$ is NH and $X^2$ is CH or $CR^{10}$; or $X^1$ is CH or $CR^{10}$ and $X^2$ is NH;

$X^3$, $X^4$ and $X^5$ are independently selected from $CR^3$ or N;

W is O or S;

$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—,
halo-$C_1$-$C_2$-alkyl, where halo is F or Cl,
halo-$C_3$-$C_4$ cycloalkyl,
halo-$C_1$-$C_2$ alkoxy, and
halo-$C_1$-$C_2$ alkylthio;

$R^2$ is selected from the group consisting of:
H,
halo,
$C_1$-$C_4$ alkyl,
$C_1$-$C_4$ alkoxy, and
halo-$C_1$-$C_2$-alkyl, where halo is F or Cl, and
cyano;

$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H, $C_1$-$C_6$ alkyl, $C_{1-4}$ hydroxyalkyl, $C_{1-4}$ fluoroalkyl or $R^4$ and $R^5$ can be taken together with the carbon to which they are attached to form a $C_3$-$C_7$ cycloalkyl ring;

AA is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from a single bond, —O—, —S—,

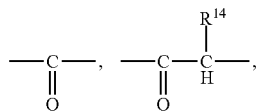

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O)— and —C(=O)NH—, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, (C=O)$OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl, $R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—(CR$^{14}$R$^{14}$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;
$R^{13}$ is independently, at each occurrence, selected from the group consisting of H, $C_1$-$C_6$ alkyl and —(CH$_2$) phenyl;
$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —(CH$_2$)$_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_1$-$C_4$-alkoxy, and halo-$C_1$-$C_4$-alkoxy
or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

2. The compound of claim 1, or a stereoisomer, tautomer, pharmaceutically acceptable salt, solvate or prodrug thereof, wherein:

$X^1$ is O and $X^2$ is CH, $CR^{10}$, or N; or $X^1$ is N and $X^2$ is O; or $X^1$ is N and $X^2$ is S;

$X^3$, $X^4$ and $X^5$ are independently selected from $CR^3$ or N; W is O;

$R^1$ is independently selected from the group consisting of:
  halo,
  $C_1$-$C_4$ alkyl,
  $C_1$-$C_4$ alkoxy,
  $C_1$-$C_4$ alkylthio,
  halo-$C_1$-$C_2$-alkyl, where halo is F or Cl, $R^2$ is H;

$R^3$ is selected from the group consisting of $C_1$-$C_4$ alkoxy, $C_1$-$C_4$ alkylthio, halo, $OCF_3$, $OCHF_2$, $OCH_2F$, or halo-$C_1$-$C_3$-alkyl;

$R^4$ and $R^5$ are independently selected from H, $C_1$-$C_6$ alkyl, $C_1$-$C_4$ fluoroalkyl or $R^4$ and $R^5$ can be taken together with the carbon to which they are attached to form a $C_3$-$C_7$ cycloalkyl ring;

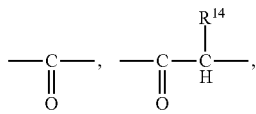

is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from a single bond, —O—, —S—, $$-\underset{\underset{O}{\parallel}}{C}-,\quad -\underset{\underset{O}{\parallel}}{C}-\underset{\underset{H}{|}}{\overset{R^{14}}{C}}-,$$

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl, $R^{11}$ and $R^{12}$ are independently, at each occurrence, selected from the group consisting of:
  H,
  $C_1$-$C_4$ alkyl,
  halo-$C_1$-$C_4$-alkyl,
  $C_2$-$C_4$ alkenyl,
  $C_2$-$C_4$ alkynyl,
  —(CR$^{14}R^{14}$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
  —(CHR$^{13}$)$_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
  —(CHR$^{13}$)$_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
  —(CHR$^{13}$)$_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —($CH_2$)phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —($CH_2$)$_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_1$-$C_4$-alkoxy, and halo-$C_1$-$C_4$-alkoxy or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

3. The compound of claim 2, or a stereoisomer, tautomer, pharmaceutically acceptable salt, solvate or prodrug thereof, wherein:

$X^1$ is O and $X^2$ is CH or N; or
$X^1$ is N and $X^2$ is O; or
$X^1$ is N and $X^2$ is S;
$X^3$, $X^4$ and $X^5$ are each $CR^3$;
W is O;
$R^1$ is independently selected from the group consisting of:
halo,
$C_1$-$C_4$ alkyl,
$C_1$-$C_4$ alkoxy, and
halo-$C_1$-$C_2$-alkyl, where halo is F or Cl;
$R^2$ is H;
$R^3$ is selected from the group consisting of H, $C_1$-$C_4$ alkoxy, $OCF_3$, $OCHF_2$, $OCH_2F$, and halo-$C_1$-$C_3$-alkyl;
$R^4$ and $R^5$ are independently selected from H, and $C_1$-$C_6$ alkyl;

is selected from the group consisting of a phenyl ring, a 5-membered heteroaryl ring containing at least one O, N or S atom, or a 6-membered heteroaryl ring, containing at least one nitrogen atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where
D is a linker, which is selected from a single bond, —O—, —S—, O,

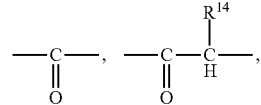

$C_1$-$C_4$ alkylene, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O)—, —C(=O)NH—, and $C_2$-$C_6$ alkenylene, B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$;

$R^b$, $R^c$, $R^d$ and $R^e$, at each occurrence, are independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^{11}R^{12}$, $N(R^{13})(C=O)NR^{11}R^{12}$, $N(R^{13})(C=O)OR^{14}$, $SO_2R^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; di-$C_1$-$C_4$-alkylamino-$C_1$-$C_4$-alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

$R^{10}$ is selected from the group consisting of $C_1$-$C_4$ alkyl, halo, cyano, $C_1$-$C_4$ alkoxy, and halo-$C_1$-$C_2$-alkyl, where halo is F or Cl;

$R^{11}$ and $R^{12}$ are independently, at each occurrence, selected from the group consisting of:

H, $C_1$-$C_4$ alkyl, halo-$C_1$-$C_4$-alkyl,

—$(CR^{14}R^{14})_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, —$(CHR^{13})_n$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, —$(CHR^{13})_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl, —$(CHR^{13})_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, hydroxy-$C_1$-$C_4$-alkyl, cyano-$C_1$-$C_4$-alkyl, $C_1$-$C_4$-alkoxy-$C_1$-$C_4$-alkyl, and alternatively, $R^{11}$ and $R^{12}$, when attached to the same nitrogen, combine to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, and —$(CH_2)_n$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, cyano, oxo, $C_1$-$C_3$ alkyl, hydroxy-$C_1$-$C_3$-alkyl, and halo-$C_1$-$C_4$-alkyl;

or $R^6$ and $R^7$ can be taken together with the carbons to which they attach to form a $C_6$-$C_{10}$ aryl ring;

n, at each occurrence, is selected from 0, 1, 2, 3, 4 or 5; and p, at each occurrence, is selected from 0, 1 and 2.

4. The compound of claim 3, or a stereoisomer, tautomer, pharmaceutically acceptable salt, solvate or prodrug thereof, wherein:

$X^1$ is O and $X^2$ is CH;

$X^3$, and $X^5$ are each CH, and $X^4$ is $CR^3$;

W is O;

$R^1$ is independently selected from the group consisting of: $CH_3$, $CH_2CH_3$, $CF_2CH_3$, $CHFCH_3$, and $OCH_3$;

$R^2$ is H;

$R^3$ is $OCH_3$;

$R^4$ and $R^5$ are H;

(AA)

is selected from the group consisting of phenyl, pyridyl, pyrimidinyl, pyrazinyl, and thiazolyl;

$R^6$ is selected from the group consisting of phenyl, cyclopentyl, cyclohexyl, pyridyl, morpholinyl, thiomorpholinyl, azetidinyl, pyrrolidinyl, piperidinyl, piperazinyl, azepanyl, tetrahydropyranyl, tetrahydrofuranyl, thiazolyl, oxazolyl, isoxazolyl, pyrazolyl, and imidazolyl, all of which may be optionally substituted with one or more $R^b$, $R^c$, $R^d$ and $R^e$;

$R^b$, $R^c$, $R^d$ and $R^e$, at each occurrence, are independently selected from halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkylsulfonyl, $C_1$-$C_4$ alkylsulfinyl, $S(=O)_2NR^{11}R^{12}$, $N(R^{13})$(C=O)$NR^{12}$, $N(R^{13})$(C=O)$OR^{14}$, $SO_2R^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and a $C_1$-$C_5$ alkyl substituted by 0 to 7 groups independently selected from halo and OH;

$R^{11}$ and $R^{12}$ are independently, at each occurrence, selected from the group consisting of:

H, $C_1$-$C_4$ alkyl, halo-$C_1$-$C_4$-alkyl, cyclopropyl, cyclopropylmethyl, hydroxy-$C_1$-$C_4$-alkyl, cyano-$C_1$-$C_4$-alkyl, $C_1$-$C_4$-alkoxy-$C_1$-$C_4$-alkyl, oxetanyl, tetrahydrofuranyl, and alternatively, $R^{11}$ and $R^{12}$, when attached to the same nitrogen, combine to form an azetidine, pyrrolidine, piperidine, or azepane ring, substituted by 0 to 2 groups independently selected from the group consisting of halo, cyano, $CF_3$, $CHF_2$, $OCF_3$, $OCHF_2$, $OCH_2F$, OH, oxo, $C_1$-$C_4$ alkyl and $C_1$-$C_4$ alkoxy;

$R^{13}$ is independently, at each occurrence, selected from the group consisting of H, and $CH_3$;

$R^{14}$ is independently, at each occurrence, selected from the group consisting of H, and $CH_3$; $R^7$ is selected from the group consisting of H, F, or $CH_3$;

n, at each occurrence, is selected from 0, 1, or 2; and p, at each occurrence, is selected from 0, 1 and 2.

5. The compound of claim 4, or a stereoisomer, tautomer, pharmaceutically acceptable salt, solvate or prodrug thereof, wherein W is O.

6. The compound of claim 5, or a stereoisomer, tautomer, pharmaceutically acceptable salt, solvate or prodrug thereof, wherein the compound of formula I is of Formula Ia.

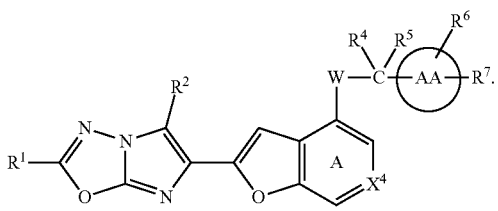

Ia

7. The compound of claim 6, or a stereoisomer, tautomer, pharmaceutically acceptable salt, solvate or prodrug thereof, wherein:
wherein $R^1$ is $C_{1-3}$alkyl;
W is O;
$X^4$ is $CR^3$ or CH;
$R^3$ is $C_1$-$C_4$ alkoxy;
$R^4$ and $R^5$ are H;

is phenyl or thiazolyl, wherein the thiazolyl is substituted with $R^6$;
$R^6$ is H or B-D:
D is a single bond;
B is phenyl which may be optionally substituted with $R^b$;
$R^b$ is $(C=O)NR^{11}R^{12}$;
$R^{11}$ and $R^{12}$ are independently, at each occurrence, selected from the group consisting of:
H,
$C_1$-$C_4$ alkyl.

8. The compound of claim 7, or a stereoisomer, tautomer, pharmaceutically acceptable salt, solvate or prodrug thereof, wherein:
$R^2$ is H.

9. The compound of claim 8, or a stereoisomer, tautomer, pharmaceutically acceptable salt, solvate or prodrug thereof, wherein:
$R^1$ is independently selected from the group consisting of: $CH_3$ and $CH_2CH_3$.

10. The compound of claim 9, or a stereoisomer, tautomer, pharmaceutically acceptable salt, solvate or prodrug thereof, wherein:

is selected from the group consisting of phenyl, pyrimidinyl, and thiazolyl; $R^6$ is phenyl, morpholinyl, piperidinyl, all of which may be optionally substituted with one or more $R^b$, $R^c$, $R^d$ and $R^e$.

11. The compound of claim 10, or a stereoisomer, tautomer, pharmaceutically acceptable salt, solvate or prodrug thereof, wherein:
$R^b$, $R^c$, $R^d$ and $R^e$, at each occurrence, are independently selected from OH, fluoro, chloro, $(C=O)NR^{11}R^{12}$, COOH, and $(C=O)OR^{14}$;
$R^{11}$ and $R^{12}$ are independently, at each occurrence, selected from the group consisting of H;
$C_1$-$C_4$ alkyl, halo-$C_1$-$C_4$-alkyl, hydroxy-$C_1$-$C_4$-alkyl, oxetanyl, and tetrahydrofuranyl; or
$R^{13}$ is independently, at each occurrence, selected from the group consisting of H, and $CH_3$;
$R^{14}$ is independently, at each occurrence, selected from the group consisting of H, and $CH_3$, and
$R^7$ is selected from the group consisting of H, F, or $CH_3$.

12. The compound as defined in claim 1, wherein the compound or salt thereof, is selected from
6-(4-(benzyloxy)-6-methoxybenzofuran-2-yl)-2-ethyl-imidazo[2,1-b][1,3,4]oxadiazole;
4-(4-(((2-(2-ethylimidazo[2,1-b][1,3,4]oxadiazol-6-yl)-6-methoxybenzofuran-4-yl)oxy)methyl)thiazol-2-yl)-N,N-dimethylbenzamide;
6-(4-(benzyloxy)-6-methoxybenzofuran-2-yl)-2-methyl-imidazo[2,1-b][1,3,4]oxadiazole; and
4-(4-(((6-methoxy-2-(2-methylimidazo[2,1-b][1,3,4]oxadiazol-6-yl)benzofuran-4-yl)oxy)methyl)thiazol-2-yl)-N,N-dimethylbenzamide.

13. A pharmaceutical composition, which comprises a pharmaceutically acceptable carrier and a compound as defined in claim 1, or stereoisomers, tautomers, pharmaceutically acceptable salts, or solvates thereof, alone or in combination with another therapeutic agent.

14. A method for the treatment of a thromboembolic disorder or the primary or secondary prophylaxis of a thromboembolic disorder, which comprises the steps of administering to a patient in need thereof a therapeutically effective amount of a compound as defined in claim 1, or stereoisomers, tautomers, pharmaceutically acceptable salts, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

15. A method of inhibiting or preventing platelet aggregation, which comprises the step of administering to a subject in need thereof a therapeutically effective amount of a PAR4 antagonist, as defined in claim 1.

\* \* \* \* \*

UNITED STATES PATENT AND TRADEMARK OFFICE
CERTIFICATE OF CORRECTION

PATENT NO. : 9,617,279 B1
APPLICATION NO. : 14/747037
DATED : April 11, 2017
INVENTOR(S) : Xiaojun Zhang et al.

Page 1 of 1

It is certified that error appears in the above-identified patent and that said Letters Patent is hereby corrected as shown below:

In the Claims

In Column 78, Line 17, In Claim 3, after "—S—," delete "O,"

In Column 80, Lines 31-32, In Claim 4, delete "$N(R^{13})(C=O)NR^{12}$," and insert -- $N(R^{13})(C=O)NR^{11}R^{12}$," --

Signed and Sealed this
Eleventh Day of December, 2018

Andrei Iancu
*Director of the United States Patent and Trademark Office*